United States Patent
Lee et al.

(10) Patent No.: US 10,571,468 B2
(45) Date of Patent: Feb. 25, 2020

(54) MODIFIED FC GAMMA RECEPTOR TYPE III (FCγIII, HNA-1) POLYPEPTIDES AND THE USES THEREOF

(71) Applicant: ONE LAMBDA, Canoga Park, CA (US)

(72) Inventors: Jar-How Lee, Los Angeles, CA (US); Neng Jen Remi Shih, Winnetka, CA (US); Julie Nguyen, Canyon Country, CA (US); Rui Pei, West Hill, CA (US)

(73) Assignee: ONE LAMBDA, INC., West Hills, CA (US)

( * ) Notice: Subject to any disclaimer, the term of this patent is extended or adjusted under 35 U.S.C. 154(b) by 348 days.

(21) Appl. No.: 15/308,521

(22) PCT Filed: May 7, 2015

(86) PCT No.: PCT/US2015/029588
§ 371 (c)(1),
(2) Date: Nov. 2, 2016

(87) PCT Pub. No.: WO2015/171847
PCT Pub. Date: Nov. 12, 2015

(65) Prior Publication Data
US 2017/0089895 A1   Mar. 30, 2017

Related U.S. Application Data

(60) Provisional application No. 61/991,145, filed on May 9, 2014.

(51) Int. Cl.
| | | |
|---|---|---|
| C07K 1/00 | (2006.01) | |
| A23J 1/00 | (2006.01) | |
| G01N 33/566 | (2006.01) | |
| G01N 33/564 | (2006.01) | |
| C07K 14/735 | (2006.01) | |
| C07K 16/00 | (2006.01) | |

(52) U.S. Cl.
CPC ..... *G01N 33/566* (2013.01); *C07K 14/70535* (2013.01); *G01N 33/564* (2013.01); *G01N 2333/4728* (2013.01); *G01N 2800/245* (2013.01)

(58) Field of Classification Search
None
See application file for complete search history.

(56) References Cited

U.S. PATENT DOCUMENTS

| | | |
|---|---|---|
| 2004/0009528 A1 | 1/2004 | Shaw et al. |
| 2007/0037195 A1 | 2/2007 | Ho |
| 2009/0142762 A1 | 6/2009 | Lee et al. |
| 2010/0055706 A1 | 3/2010 | Greinacher et al. |
| 2012/0263711 A1 | 10/2012 | Stavenhagen et al. |

FOREIGN PATENT DOCUMENTS

| | | |
|---|---|---|
| EP | 2052713 A2 | 4/2009 |
| WO | WO-1990/14363 A1 | 11/1990 |

OTHER PUBLICATIONS

Altschul et al., Basic local alignment search tool, J. Mol. Biol., 215(3):403-10 (1990).
Bix et al., Functionally conformed free class I heavy chains exist on the surface of beta 2 microglobulin negative cells, J. Exp. Med., 176(3):829-34 (1992).
Bux et al., Analysis of granulocyte-reactive antibodies using an immunoassay based upon monoclonal-antibody-specific immobilization of granulocyte antigens, Transfus. Med., 3(2):157-62 (1993).
Cao et al., Raman dye-labeled nanoparticle probes for proteins, J. Am. Chem. Soc., 125:14676-7 (2003).
Choo, The HLA system: genetics, immunology, clinical testing, and clinical implications, Yonsei Med. J., 48(1):11-23 (2007).
Chu et al., SV40 DNA transfection of cells in suspension: analysis of efficiency of transcription and translation of T-antigen, Gene, 13(2):197-202 (1981).
Davoren et al., TRALI due to granulocyte-agglutinating human neutrophil antigen-3a (5b) alloantibodies in donor plasma: a report of 2 fatalities, Transfusion, 43(5):641-5 (2003).
Devereux et al., A comprehensive set of sequence analysis programs for the VAX, Nucleic Acids Res., 12(1 Pt 1):387-9 (1984).
Elghanian et al., Selective colorimetric detection of polynucleotides based on the distance-dependent optical properties of gold nanoparticles, Science, 277(5329):1078-81 (1997).
Graham et al., A new technique for the assay of infectivity of human adenovirus 5 DNA, Virology, 52(2):456-67 (1973).
Hibbs et al., Membrane-proximal Ig-like domain of Fc gamma RIII (CD16) contains residues critical for ligand binding, J. Immunol., 152(9):4466-74 (1994).
International Preliminary Report on Patentability, International Application No. PCT/US2015/029588, dated Nov. 15, 2016.
International Search Report and Written Opinion, International Application No. pCT/US15/29588, dated Nov. 6, 2015.
Jayasena, Aptamers: an emerging class of molecules that rival antibodies in diagnostics, Clin. Chem., 45(9):1628-50 (1999).
Kitts et al., A method for producing recombinant baculovirus expression vectors at high frequency, Biotechniques, 14(5):810-7 (1993).
Kobayashi et al., Autoimmune neutropenia in infancy due to anti-NA1 antibody: detection of antibody with immunofluorescence and agglutination test, Pediatr. Res., 26(3):246-9 (1989).
Krangel et al., Assembly and maturation of HLA-A and HLA-B antigens in vivo, Cell, 18(4):979-91 (1979).
Luckow et al., Efficient generation of infectious recombinant baculoviruses by site-specific transposon-mediated insertion of foreign genes into a baculovirus genome propagated in *Escherichia coli*, J. Virol., 67(8):4566-79 (1993).

(Continued)

*Primary Examiner* — Chun W Dahle
(74) *Attorney, Agent, or Firm* — One Lambda, Inc.; Greg Kline

(57) ABSTRACT

The invention is directed to engineered Fc gamma receptor type III (Fcγ111, HNA-1) polypeptides and use of these polypeptides to detect antibodies specific for human neutrophil antigens (HNA). The invention is also directed to methods for the diagnosing and determining susceptibility for developing Transfusion Reaction Acute Lung (TRALI).

6 Claims, 9 Drawing Sheets
Specification includes a Sequence Listing.

(56) References Cited

OTHER PUBLICATIONS

Mair et al., the role of fatigue in susceptibility to acute muscle strain injury, Am. J. Sports Med., 24(2):137-43 (1996).
Marsh et al., Nomenclature for factors of the HLA system, 2000, Hum. Immunol., 62(4):419-68 (2001).
Metcalfe et al., Location of the granulocyte-specific antigen LAN on the Fc-receptor III, Transfus. Med., 2(4):283-7 (1992).
Nam et al., Nanoparticle-based bio-bar codes for the ultrasensitive detection of proteins, Science, 301(5641):1884-6 (2003).
Park et al., Array-based electrical detection of DNA with nanoparticle probes, Science, 295(5559):1503-6 (2002).
Pei et al., Detection of antibodies against β-microglobulin free HLA heavy chains using FlowPRA beads, Visuals Clinical Histocompatability Workshop, pp. 9-10 (2000).
Popovsky et al., Diagnostic and pathogenetic considerations in transfusion-related acute lung injury, Transfusion, 25(6):573-7 (1985).
Schnabl et al., Activated human T lymphocytes express MHC class I heavy chains not associated with beta 2-microglobulin, J. Exp. Med., 171(5):1431-42 (1990).
Snyder et al., The role of cytokines and adhesive molecules in febrile non-hemolytic transfusion reactions, Immunol. Invest., 24(1-2):333-9 (1995).
Sugawara et al., A simple method to eliminate the antigenicity of surface class I MHC molecules from the membrane of viable cells by acid treatment at pH 3, J. Immunol. Methods, 100(1-2):83-90 (1987).
Tamm et al., The IgG binding site of human FcgammaRIIIB receptor involves CC' and FG loops of the membrane-proximal domain, J. Biol. Chem., 271(7):3659-66 (1996).
Taton et al., Scanometric DNA array detection with nanoparticle probes, Science, 289(5485):1757-60 (2000).
Taton et al., Two-color labeling of oligonucleotide arrays via size-selective scattering of nanoparticle probes, J. Am. Chem. Soc., 123(21):5164-5 (2001).
Uchiyama et al., Cellular adhesion molecules, Transfus. Med. Rev., 8(2):84-95 (1994).
Uniprot Accession No. O75015, Low affinity immunoglobulin gamma Fc region receptor III-B, FCGR3B.
Urlaub et al., Isolation of Chinese hamster cell mutants deficient in dihydrofolate reductase activity, Proc. Natl. Acad. Sci. USA, 77(7):4216-20 (1980).
EBI Accession No. EPOP:GN348789, "Sequence 25 from Patent EP2052713" (May 7, 2009).
EBI Accession No. GSP:AD039745, Immunoglobulin G-binding receptor #1 (Jul. 15, 2004).
EBI Accession No. GSP:BBW37832, "Human Fc gamma RIIIa polypeptide mutant T163S" (May 21, 2015).
EBI Accession No. USPOP:AAN88660, Sequence 7 from patent U.S. Pat. No. 6,444,789 (Dec. 20, 2002).
European Patent Application No. 15789983.2, Communication Pursuant to Article 94(3) EPC, dated Oct. 30, 2018.
European Patent Application No. 15789983.2, Extended European Search Report, dated Nov. 29, 2017.
Muschter et al., Developments in the definition and clinical impact of human neutrophil antigens, Curr. Opin. Hematol., 18(6):452-60 (Nov. 2011).
Reil et al., HNA-1d: a new human neutrophil antigen located on Fc? receptor IIIb associated with neonatal immune neutropenia, Transfusion, 53(10):2145-51 (Oct. 2013).

MODIFIED FC GAMMA RECEPTOR TYPE III (FCγIII, HNA-1) POLYPEPTIDES AND THE USES THEREOF

FIELD OF INVENTION

The invention is directed to engineered Fc gamma receptor type III (FcγIII, HNA-1) polypeptides and use of these polypeptides to detect antibodies specific for human neutrophil antigens (HNA). The invention is also directed to methods for the diagnosing and determining susceptibility for developing transfusion reaction acute lung (TRALI).

BACKGROUND

TRALI is a common clinical complication of transfusion. It is the leading cause of transfusion-related death in the United States. TRALI usually develops within 6 hours of transfusion. However, it can be observed within 1~2 hours after transfusion. Symptoms of TRALI consist of the rapid onset of tachypnea, cyanosis, dyspnea, and fever. TRALI syndrome is difficult to diagnose, because initially it shares similar symptoms with transfusion-independent lung insufficiency (ALI) or ARDS ("acquired respiratory distress syndrome") (Popovsky & Moore, Transfusion 25:573-577, 1985). TRALI is often misdiagnosed in the clinic because the symptoms are attributed to fluid overload. TRALI has been associated with the transfusions of all plasma related components, including whole blood, red blood concentrates, fresh frozen plasma, whole blood derived from platelets, pooled platelets, intravenous gamma-globulin, cryoprecipitate, stem cells and granulocytes. Because TRALI affects the pulmonary microvascular tissue, treatment focuses on respiratory support and saline infusion. The mortality rate from TRALI ranges from 5% to 25%. In North America, a case of TRALI happens 1 per 5,000 to 1 per 1,323 transfusions. Most patients recover within 72 hours; however, data for TRALI are limited, and the reported morbidity and mortality rate may be underestimated because of lack of recognition and underreporting.

TRALI is primarily associated with antibodies specific for HNA, granulocyte- and human leukocyte antigens (HLA) Class I and Class II. Other factors known to induce TRALI in transfusion recipients include biologically active lipids. In most cases, antibodies of the donor (in the donor plasma) react with the leucocytes (granulocytes) of the recipient. Binding of antibodies to the granulocytes activates the granulocytes and leads to aggregation. Oxygen radicals, cytokines, and proteases are released from the complement-activated granulocytes, damaging the capillary endothelium and causing. Extravasation of protein-rich fluid into the pulmonary alveoli and interstitium. In addition, the donor antibodies also bind to and activate granulocytes, of the recipient, and stimulate the expression of adhesion molecules (Uchiyama et al. Transfus. Med. Rev. 8:84-95, 1994). The immunological response also causes transmigration of granulocytes into the interstitial space between alveolar and vessel endothelium of the lung. (Snyder, Immol Invest. 24:333-9, 1994). These cellular effects cause damage to the capillary walls with subsequent hyperpermeability. A lung edema develops and 10% of the affected patients die from this complication.

A high percentage of TRALI cases are caused by blood donated by females, particularly multiparous women, because pregnant women can develop antibodies against granulocyte- or HLA-antigens of the child. A patient may be also immunized as the result of an earlier transfusion (Voss et al., Anaesthesist 50:930-932, 2001). Proposed current solutions for reducing the incidence of TRALI include the exclusion of all female donors, or at least the exclusion of multiparous (three or more pregnancies) female donors, and/or reducing the transfusion of fresh, frozen plasma.

Most blood and tissue donors have not been typed for HNA. Currently, the detection of granulocyte-specific antibodies is laborious; and detection of HNA antibodies in the serum of the blood donor is not sufficient. The requirement for lab technicians specialized in the nature of neutrophils, the lack of available HNA typing sera and the need to provide fresh neutrophils make typing HNA on a larger scale impractical, if not impossible, for most laboratories. Currently, the most reliable determination of TRALI risk is cross-matching between donor serum and patient leucocytes. This test can be carried out only in specialized laboratories (Voss, Anaesthesist 50:930-932, 2001) which are not suitable for donor screening. Other strategies include donor restriction management (Mair et al., Crit. Care Med. 34:137-143, 2006), causing significant reduction in the amount of stored blood because it excludes women from blood donation after pregnancy.

There is a need for more sensitive methods of detecting HNA specific antibodies in biological samples which will assist in predicting the risk of the transfusion or transplant recipient developing TRALI.

SUMMARY OF INVENTION

The invention provides for methods of generating a modified polypeptide having affinity to an Fc receptor comprising substituting one or more amino acids within one or more Fc binding domains of the polypeptide wherein the substitution (i) decreases non-specific reactivity of the polypeptide and (ii) increases the specific reactivity of the polypeptide with an antibody that specifically binds said polypeptide.

The methods may be carried out with a polypeptide having affinity for an Fc receptor selected from the group consisting of FcγI (CD64), FCγRIIA (CD32), FCγRIIB (CD32), FcγIIIA (CD16a), FCγRIIIB (CD16b), FcRn, FcεRI and FcεRII (CD23), FcεRI and Fcα/μR. The methods of the invention may be carried out with a polypeptide that is an antibody or fragment thereof, in particular the antibody may be a secondary antibody used in assays to detect primary antibody binding.

The present invention also relates to methods of generating polymorphic Fc gamma receptor type IIIb (FcγRIIIb, CD16b, HNA-1) polypeptides having a modified Fc binding region, wherein said modified Fc binding region comprises at least one amino acid modification relative to the wild-type. These modified polypeptides reduce the nonspecific antibody (IgG) binding to the Fc binding region, and thereby increase the detectable range sensitivity of anti-polymorphic Fc receptor type IIIb (FcγRIIIb, CD16b, HNA-1) antibodies.

The present invention also provides for the methods of detecting HNA-1 specific antibodies, such as antibodies that specifically bind HNA-1a, HNA-1b or HNA-1c present in donor tissue intended for transplants or transfusion in order to determine whether the donor tissue, as a result of the presence of any anti-HNA specific antibodies, will induce TRALI or graph versus host disease (GVHD) in a human recipient that expresses the different polymorphic HNA molecules.

The wild type Fc gamma receptor type Mb polypeptide (Uniprot Accession No. O75015) is set out as SEQ ID NO: 1. The wild type FC gamma receptor has three Fc binding domain regions. The FC binding domain 1 spans amino acids 131 to 138 of SEQ ID NO: 1 (WKNTALHK; SEQ ID NO: 2). The Fc binding domain 2 spans amino acids 150 to 154 of SEQ ID NO: 1 (YFHHN; SEQ ID NO: 3). The Fc binding domain 3 spans amino acids 175 to 181 of SEQ ID NO: 1 (LVGSKNV; SEQ ID NO: 3). The modified polypeptides of the invention have one more amino acids modification within in at least one of the Fc binding domains.

In one aspect, the invention provides for methods of generating a modified HNA-1 polypeptide of SEQ ID NO: 1 comprising substituting one or more amino acids within one or more FC binding domains wherein the substitution (i) decreases the non-specific reactivity of the modified polypeptide and (ii) increases the specific reactivity of the modified HNA-1 polypeptide with an HNA-1 specific antibody or an HNA-1 polymorphic HNA-1 antibody. The modified HNA-1 polypeptides may be generated by substituting one or more amino acids in a single FC binding domain or multiple substitutions within multiple FC binding domains within a single polypeptide.

The term "HNA-1 specific antibody" refer to an antibody that binds to any HNA-1 antigen and may bind more than one HNA-1 polymorphs. The term "HNA-1 polymorphic specific antibody" refers to an antibody that specifically binds a particular HNA-1 polymorph such as an antibody that specifically binds HNA-1a, HNA-1b or HNA-1c.

For example, the methods of the invention generate HNA-1 modified polypeptides by substituting at least one amino acid within the FC binding domain 1 of SEQ ID NO: 1, such as methods wherein the substitution is selected from the group consisting of the lysine at residue 132 substituted with phenylalanine (K132F), the lysine at residue 132 substituted with arginine (K132R), the asparagine at residue 133 substituted with phenylalanine (N133F), the threonine at residue 134 substituted with phenylalanine (T134F), the threonine at residue 134 substituted with tryptophan (T134W), the alanine at residue 135 substituted with aspartate (A135D), the lysine at residue 136 substituted with alanine (L136A), the histidine at residue 137 substituted with tyrosine (H137Y) and the lysine at residue 138 substituted with threonine (K138T).

The methods of the invention also include generating modified HNA-1 polypeptides by substituting at least one amino acid within the FC binding domain 2 of SEQ ID NO: 1, such as methods wherein the substitution is selected from the group consisting of the histidine at residue 152 substituted with tyrosine (H152Y), the histidine at residue 153 substituted with glutamate (H153E), the phenylalanine at residue 151 substituted with alanine (F151A) and the histidine at residue 153 substituted with alanine.

The methods of the invention also include generating modified HNA-1 polypeptides by substituting at least one amino acid within the FC binding domain 3 of SEQ ID NO: 1, such as methods wherein the substitution is selected from the group consisting of the valine at residue 176 substituted with alanine (V176A) and the glycine at residue 177 substituted with alanine (G177A).

The invention provides for purified Fc gamma receptor type IIIb polypeptide comprising a modified amino acid sequence or an antigenic fragment thereof, wherein at least one amino acid is modified within one or more of the FC binding domains of SEQ ID NO: 1 and wherein the modified amino acid sequence has (i) decreased non-specific reactivity and (ii) increased reactivity with HNA-1 specific antibodies or HNA-1 polymorphic specific antibodies as compared to wild-type polypeptides having the amino acid sequence of SEQ ID NO: 1. Non-specific reactivity, also known as background binding, refers to antibodies binding to areas other than their epitope. Increased reactivity is an increase in the sensitivity for binding with an HNA-1 specific antibody or an increase in the detectable range of binding between the modified polypeptide and the HNA-1 specific antibody.

Modifications or modified amino acids include amino acid substitutions, insertion and deletions within a polypeptide sequence. The modified polypeptides of the invention may comprise at least one modification, at least two modifications, at least three modification, at least four modifications or at least five modifications.

In one aspect of the invention, the modified FC gamma receptor type IIIb polypeptide has a modification within amino acids 131 to 138 of SEQ ID NO: 1, also known as Fc binding domain 1. For example, the modification is an amino acid substitution at residue 131 in which tryptophan is substituted with phenylalanine (W131F), or the modification is an amino acid substitution at residue 132 in which lysine is substituted with phenylalanine (K132F), or the modification is an amino substitution at residue 132 in which lysine is substituted with arginine (K132R), or the modification is an amino acid substitution at residue 133 in which asparagine is substituted with phenylalanine (N133F), or the modification is an amino acid substitution at residue 134 in which threonine is substituted with phenylalanine (T134F), or the modification is an amino acid substitution at residue 134 in which threonine is substituted with tryptophan (T134W), or the modification is an amino acid substitution at residue 135 in which alanine is substituted with aspartate (A135D), or the modification is an amino acid substitution at residue 136 in which leucine is substituted with alanine (L136A), or the modification is an amino acid substitution at residue 137 in which histidine is substituted with tyrosine (H137Y) or the modification is an amino acid substitution at residue at 138 in which lysine is substituted with threonine (K138T).

In another aspect of the invention, the modified FC gamma receptor type IIIb polypeptide has a modification within amino acids 150 to 154 of SEQ ID NO: 1, also known as Fc binding domain 2. For example, the modification is an amino acid substitution at residue at 151 in which phenylalanine is substituted with alanine (F151A), or the modification is an amino acid substitution at residue 152 in which histidine is substituted with tyrosine (H152Y), or the modification is an amino acid substitution at residue 153 in which histidine is substituted with glutamate (H153E), or the modification is an amino acid substitution at residue 152 or 153 phenylalanine is substituted with alanine (H152A; H153A).

In another aspect of the invention, the modified FC gamma receptor type IIIb polypeptide has a modification within amino acids 175 to 181 of SEQ ID NO: 1, also known as Fc binding domain 3. For example, the modification is an amino acid substitution at residue 176 in which valine is substituted with alanine (V176A), or the modification is an amino acid substitution at residue 177 in which glycine is substituted with alanine (G177A), or the modification is an amino acid substitution at residue 179 in which lysine is substituted with leucine (K179L), or the modification is an amino acid substitution at residue 181 in which valine is substituted with tyrosine (V181Y).

The invention contemplates modified polypeptides comprising more than one modification, for example the polypeptide may have at least one or at least two or at least three modifications in one Fc binding domain. Alternatively, the modified polypeptide may have at least one or at least two or at least three modifications that are present in more than one Fc binding domain. For example, the modified polypeptide has three amino acid substitutions within Fc binding domain 2 in which at residue 151 phenylalanine is substituted with alanine and at residue152 histidine is substituted with alanine and at residue 153 histidine is substituted with alanine (F151AH152AH153A) as set out in SEQ ID NO: 25. Another example is the modified polypeptide has two amino acid substitutions within the Fc binding domain 3 in which at residue 176 valine is substituted with alanine and at residue 177 glycine is substituted with alanine (V176AG177A) as set out in SEQ ID NO: 27.

The modified polypeptides of the invention may comprise a peptide having the amino acid sequence of SEQ ID NO: 8, SEQ ID NO: 10, SEQ ID NO: 12, SEQ ID NO:14, SEQ ID NO: 16, SEQ ID NO: 18 and SEQ ID NO: 20, SEQ ID NO: 22, SEQ ID NO: 24, SEQ ID NO: 26, SEQ ID NO: 28

The modified polypeptides of the invention include those comprising an amino acid sequence selected from the group consisting of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25 or SEQ ID NO: 27 or an antigenic fragment thereof.

The invention also provides for any of the modified polypeptides comprising a heterologous or exogenous amino acid sequence. The terms "heterologous" and "exogenous" refers to a nucleic acid or amino acid sequence that is not naturally produced by the cell or organism, for example the protein or polypeptide was derived from a different cell type or different species than the host cell. The invention also provides for any of the modified polypeptides which are recombinantly expressed.

In another embodiment, the invention provides for polynucleotides comprising a nucleotide sequence encoding any of the modified polypeptides of the invention. The term "vector" is used to refer to any molecule (e.g., nucleic acid, plasmid, or virus) used to transfer coding information to a host cell. The invention also provides for vectors and isolated host cells comprising polynucleotides encoding the modified polypeptides of the invention. In addition, the invention provides for isolated host cells comprising the polynucleotides encoding the modified polypeptides of the invention and/or vectors comprising the same. In any of the host cells or vectors of the invention, the polynucleotide may be operatively linked to a heterologous control sequence such as a promoter or enhancer.

In addition, the invention provides for host cells expressing the modified polypeptides of the invention and host cells comprising the polynucleotide sequence of the invention which is operatively linked to a heterologous control sequence such as a promoter or enhancer.

In a further embodiment, the invention also provides for solid substrates on which one or more of the modified polypeptides of the invention are attached or affixed thereto. The solid substrate may be a membrane, bead, microbead, microparticle, filter, glass, silicon, metal, metal-alloy, anopore, polymeric, nylon or plastic. The invention also provides for panels of solid substrates in which one or more modified polypeptides of the invention are attached or affixed thereto, such as a panel comprising a plurality of microbeads wherein in each microbead has one or more modified polypeptide attached or affixed to its surface. Alternatively, the panel comprising a plurality of microbeads in which each microbead has one unique modified polypeptide attached or affixed to its surface.

In another embodiment, the invention provides for methods of detecting an HNA-1 specific antibody in a biological sample comprising a) contacting a biological sample with one or more modified HNA-1 polypeptides or an antigenic fragment thereof to form a complex with the HNA-1 specific antibody, and b) detecting the complex, wherein the presence of the complex indicates that the biological sample contains HNA-1 specific antibodies. The modified HNA-1 polypeptide may be any of the modified polypeptides of the invention such as a polypeptide comprising the amino acid sequence or SEQ ID NO: 8, SEQ ID NO: 10, SEQ ID NO: 12, SEQ ID NO:14, SEQ ID NO: 16, SEQ ID NO: 18, SEQ ID NO: 20, SEQ ID NO: 22, SEQ ID NO: 24, SEQ ID NO: 26, SEQ ID NO: 28 or a polypeptide comprising the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 1, SEQ ID NO: 23, SEQ ID NO: 25 or SEQ ID NO: 27 or an antigenic fragment thereof, or a polypeptide comprising the amino acid sequence of SEQ ID NO: 6, SEQ ID NO: 30, SEQ ID NO: 32 or an antigenic fragment thereof. In these methods, the biological sample may be contacted with a cell transformed or transfected to express the modified polypeptide of the invention or an antigenic fragment thereof.

The invention also provides for methods of detecting an HNA-1 specific antibody in a biological sample, wherein in addition to detecting HNA-1 specific antibodies, the methods further comprise one or more of the following steps: contacting the biological sample the biological sample with CD177 polypeptide or an antigenic fragment thereof to form a complex with HNA-2 specific antibodies in the biological sample, contacting the biological sample with CTL2 polypeptide or an antigenic fragment thereof to form a complex with HNA-3 specific antibodies in the biological sample including antibodies specific for HNA-3a or HNA-3b, contacting the biological sample with CD11b polypeptide or an antigenic fragment thereof to form a complex with HNA-4 specific antibodies in the biological sample including HNA-4a or HNA-4b specific antibodies, contacting the biological sample with CD11a polypeptide or an antigenic fragment thereof to form a complex with HNA-5 specific antibodies in the biological sample including HNA-5a or HNA-5b specific antibodies, contacting the biological sample with an HLA antigen to form a complex with HLA specific antibodies in the biological sample, and detecting the complex or contacting the biological sample with a MICA antigen to form a complex with MICA specific antibodies in the biological sample, and detecting the complex, wherein the presence of any of the complexes indicates that the biological sample contains HNA and/or HLA and/or MICA specific antibodies.

The invention also provides for methods of determining whether the risk for a donor tissue intended for transplant or transfusion will induce transfusion related acute lung injury (TRALI) or graft versus host disease (GVHD) in a human recipient wherein the human recipient expresses an HNA-1 antigen comprising a) contacting a biological sample obtained from the donor prior to transplant or transfusion with one or more modified HNA-1 polypeptides or an antigenic fragment thereof to form a complex with HNA-1 specific antibodies in the sample, and b) detecting the complex, wherein the presence of the complex in the biological sample indicates that the donor tissue is likely to induce TRALI or GVHD in a human recipient that expresses the HNA-1 antigen. The modified HNA-1 polypeptide may be any of the modified polypeptides of the invention such as a polypeptide comprising the amino acid sequence or SEQ ID NO: 8, SEQ ID NO: 10, SEQ ID NO: 12, SEQ ID NO:14, SEQ ID NO: 16, SEQ ID NO: 18, SEQ ID NO: 20, SEQ ID NO: 22, SEQ ID NO: 24, SEQ ID NO: 26, SEQ ID NO: 28, or a polypeptide comprising the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27 or an antigenic fragment thereof, or a polypeptide comprising the amino acid sequence of SEQ ID NO: 6, SEQ ID NO: 30, SEQ ID NO: 32 or an antigenic fragment thereof.

The invention also provides for methods of determining the risk that a donor tissue intended for transplant or transfusion will induce transfusion related acute lung injury (TRALI) or graft versus host disease (GVHD) in a human recipient wherein the human recipient expresses an HNA-1 antigen, wherein in addition to detecting HNA-1 specific antibodies, the methods further comprise one of more of the following steps: contacting the biological sample with CD177 polypeptide or an antigenic fragment thereof to form a complex with HNA-2 specific antibodies in the biological sample, contacting the biological sample with CTL2 polypeptide or an antigenic fragment thereof to form a complex with HNA-3 specific antibodies in the biological sample including HNA-3a or HNA-3b specific antibodies, contacting the biological sample with CD11b polypeptide or an antigenic fragment thereof to form a complex with HNA-4 specific antibodies in the biological sample including HNA-4a or HNA-4b specific antibodies, contacting the biological sample with CD11a polypeptide or an antigenic fragment thereof to form a complex with HNA-5 specific antibodies in the biological sample including HNA-5a or HNA-5b specific antibodies, contacting the biological sample with an HLA antigen to form a complex with HLA specific antibodies in the biological sample, contacting the biological sample with a MICA antigen to form a complex with MICA specific antibodies in the biological sample, and detecting the complex, wherein the presence of any of the complexes in the biological sample indicates that the donor tissue is likely to induce TRALI or GVHD in a human recipient that expresses any of HNA-1, HNA-2, HNA-3a, HNA-3b, HNA-4a, HNA-4b, HNA-5a, HNA-5b, and HLA antigens.

Another embodiment of the invention is methods of determining the susceptibility of a human transplant or transfusion recipient for rejecting transplanted or transfused tissue, wherein the donor tissue contains HNA-1 polypeptide or an antigenic fragment thereof, comprising a) contacting a biological sample from the human transplant or transfusion recipient prior to transplantation or transfusion with a modified Fc gamma receptor type IIIb polypeptide or an antigenic fragment thereof to form a complex with HNA-1 specific antibodies in the biological sample, and b) detecting the complex, wherein the presence of the complex in the biological sample indicates that the human transplant or transfusion recipient is susceptible for rejecting the transplanted or transfused tissue. The modified Fc gamma receptor type IIIb polypeptide may be any of the modified polypeptides of the invention such as a polypeptide comprising the amino acid sequence or SEQ ID NO: 8, SEQ ID NO: 10, SEQ ID NO: 12, SEQ ID NO:14, SEQ ID NO: 16, SEQ ID NO: 18, SEQ ID NO: 20, SEQ ID NO: 22, SEQ ID NO: 24, SEQ ID NO: 26, SEQ ID NO: 28, or a polypeptide comprising the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25 or SEQ ID NO: 27 or an antigenic fragment thereof, or a polypeptide comprising the amino acid sequence of SEQ ID NO: 6, SEQ ID NO: 30 or SEQ ID NO: 32 or a fragment thereof.

The invention also provides for methods of determining the susceptibility of a human transplant or transfusion recipient for rejecting transplanted or transfused tissue, wherein the donor tissue contains HNA-1 polypeptide or an antigenic fragment thereof, wherein in addition to detecting HNA-1 specific antibodies, the methods further comprise one of more of the following steps: contacting the biological sample the biological sample with CD177 polypeptide or an antigenic fragment thereof to form a complex with HNA-2 specific antibodies in the biological sample, contacting the biological sample with CTL2 polypeptide or an antigenic fragment thereof to form a complex with HNA-3 specific antibodies in the biological sample including HNA-3a or HNA-3b specific antibodies, contacting the biological sample with CD11b polypeptide or an antigenic fragment thereof to form a complex with HNA-4 specific antibodies in the biological sample including HNA-4a or HNA-4b specific antibodies, contacting the biological sample with CD11a polypeptide or an antigenic fragment thereof to form a complex with HNA-5 specific antibodies in the biological sample including HNA-5a or HNA-5b specific antibodies, contacting the biological sample with an HLA antigen to form a complex with HLA specific antibodies in the biological sample, or contacting the biological sample with a MICA antigen to form a complex with MICA specific antibodies in the biological sample, and detecting the complex, wherein the presence of any of the complexes in the biological sample indicates that the human transplant or transfusion recipient is susceptible for rejecting the transplanted or transfused tissue.

In any of the method of the invention, the complex between the modified polypeptide of the invention or an antigenic fragment thereof and the HNA-1 specific antibody may be detected with a secondary antibody. In addition, the secondary antibody may comprises a label selected from the group consisting of a radioactive label, fluorescent label, enzymatic label, avidin label or biotin label.

In any of the methods of the invention, the tissue sample or biological sample is selected from the group consisting of blood, blood derivatives, plasma, serum, cells, and tissues. In particular, the biological sample may be neutrophils.

In addition, any of the method of the invention may be carried out with modified polypeptides of the invention and/or wild type HNA and HLA antigens that are attached or affixed to a solid substrate. The solid substrate may be a membrane, beads, microbead, microparticles, filter, glass, silicon, metal, metal-alloy, anopore, polymeric, nylon or plastic. Furthermore, any of the methods of the invention may be carried out using a panel of solid substrates in which one or more modified polypeptides of the invention or an antigenic fragment thereof are attached to the solid substrates, such as a panel comprising a plurality of microbeads wherein in each microbead has one or more modified polypeptide attached or affixed to its surface. Another example is a panel comprising a plurality of microbeads in which each microbead has one unique modified polypeptide of the invention or an antigenic fragment thereof attached or affixed to its surface.

Another embodiment of the invention is kits comprising one or more modified polypeptides of the invention or an antigenic fragment thereof and optionally comprising a polypeptide of SEQ ID NO: 1 or an antigenic fragment thereof. In particular, the invention provides for kits for detecting HNA-1 antibodies in a biological sample, kits for determining the susceptibility of a human transplant or transfusion recipient for rejecting transplanted or transfused tissue, wherein the donor tissue contains HNA-1 polypeptide or an antigenic fragment thereof and kits for determining the risk for whether a donor tissue intended for transplant or transfusion will induce transfusion related acute lung injury (TRALI) or graft versus host disease (GVHD) in a human recipient wherein the human recipient expresses an HNA-1 antigen.

The kits of the invention comprise one or more modified polypeptides of the invention such as such as a polypeptide comprising the amino acid sequence or SEQ ID NO: 8, SEQ ID NO: 10, SEQ ID NO: 12, SEQ ID NO:14, SEQ ID NO: 16, SEQ ID NO: 18, SEQ ID NO: 20, SEQ ID NO: 22, SEQ ID NO: 24, SEQ ID NO: 26, SEQ ID NO: 28, or a polypeptide comprising the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27 or an antigenic fragment thereof. The kits may also comprise one or more polypeptides or antigenic fragments thereof selected from the group consisting of wild type of Fc-γ receptor Mb polypeptide, other modified HNA-1 polypeptides such polypeptides comprising the amino acid sequence of SEQ ID NO: 6, SEQ ID NO: 30, SEQ ID NO: 32 or a fragment thereof, CD177 polypeptide (HNA-2), CTL2 polypeptide (HNA-3a and HNA_3 b), CD11b polypeptide (HNA-4), CD11a polypeptide (HNA-5), an HLA antigen and a MIC A antigen.

The kits may optionally further comprise an HNA-1 specific antibody and one or more antibodies that specifically bind a peptide comprising an antigen HNA-2, HNA-3a, HNA-3b, HNA-4, HNA-5 or HLA.

The invention provides for a use of the modified polypeptides of the invention or antigenic fragments thereof for the identification of HNA-1 specific alloantibodies.

The invention also provides for a use of the modified polypeptides of the invention or antigenic fragments thereof which react with HNA-1 specific alloantibodies in the analysis of blood samples, plasma sample or serum sample for identification of HNA-1 specific antibodies.

The invention also provides for a use of the modified polypeptides of the invention or antigenic fragments thereof in a process, which uses the polypeptide or fragment thereof to separate antibodies from blood sample, plasma sample or serum sample.

Another aspect of the present application relates to a method for preparing a blood composition for reducing a transfusion related etiology, including but not limited to TRALI, transfusion related autoimmune neutropenia and febrile reactions. Thus, in one embodiment a modified polypeptide of the invention is utilized to treat blood products prior to transfusion. The blood product may then be suitable for introducing into a recipient. In some embodiments, a method of depleting a blood sample of anti-HNA antibodies is disclosed, the method encompassing contacting the blood sample with one or more modified HNA polypeptides of the invention or fragments thereof such as a modified HNA-1 polypeptide of the invention, optionally attached to a solid support and depleting the antibodies bound to the modified HNA polypeptides or fragments thereof. "Depleting" refers to reduction of said antibodies by 10%, 20%, 30%, 50% or more relative to a control untreated with the modified HNA polypeptide. For example, the modified HNA-1 polypeptide utilized in the preceding methods of preparing a blood composition for reducing a transfusion related etiology or methods of depleting a blood sample of anti-HNA antibodies may be any of the modified polypeptides of the invention such as a polypeptide comprising the amino acid sequence or SEQ ID NO: 8, SEQ ID NO: 10, SEQ ID NO: 12, SEQ ID NO:14, SEQ ID NO: 16, SEQ ID NO: 18, SEQ ID NO: 20, SEQ ID NO: 22, SEQ ID NO: 24, SEQ ID NO: 26, SEQ ID NO: 28, or a polypeptide comprising the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27 or an antigenic fragment thereof, or a polypeptide comprising the amino acid sequence of SEQ ID NO: 6, SEQ ID NO: 30, SEQ ID NO: 32 or an antigenic fragment thereof.

In addition, any of the method of the invention may be carried out with modified polypeptides of the invention and/or wild type HNA and HLA antigens that are attached or affixed to a solid substrate. The solid substrate may be a membrane, beads, microbead, microparticles, filter, glass, silicon, metal, metal-alloy, anopore, polymeric, nylon or plastic. Furthermore, any of the methods of the invention may be carried out using a panel of solid substrates in which one or more modified polypeptides of the invention or an antigenic fragment thereof are attached to the solid substrates, such as a panel comprising a plurality of microbeads wherein in each microbead has one or more modified polypeptide attached or affixed to its surface. Another example is a panel comprising a plurality of microbeads in which each microbead has one unique modified polypeptide of the invention or an antigenic fragment thereof attached or affixed to its surface.

In other embodiments, a composition is disclosed. The composition encompassing blood or a blood product depleted of antibodies specific to HNA. In some embodiments, the blood product encompasses platelets. In some embodiments, the blood product encompasses packed red blood cells. In other embodiments, the blood product encompasses plasma.

The invention provides for a method of detecting an HNA-1 specific antibody in a biological sample comprising a) contacting the biological sample with an aptamer that mimics an antigenic fragment of a modified polypeptide of the invention to form a complex with the HNA-1 specific antibodies in the sample, and b) detecting the complex, wherein the presence of the complex indicates that the biological sample contains HNA-1 specific antibodies.

DETAILED DESCRIPTION

Figure 1:
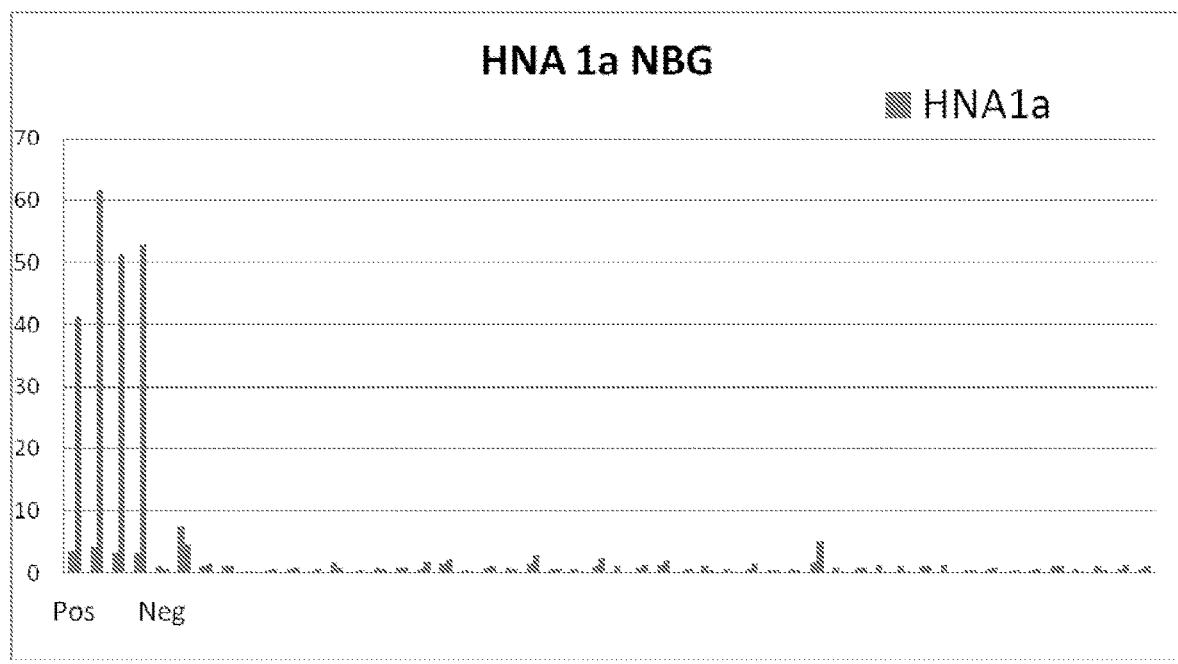
FIG. 1 depicts the improvement of detection sensitivity for HNA-1 specific antibodies by HNA-1a modified polypeptides having the L136A substitution compared to wild-type HNA-1a polypeptide.

The invention is directed to the methods of screening for antibodies specific for human neutrophil antigen-1 (HNA-1). HNA-1 belongs to Fc gamma receptor type IIIb (FcγRIIIb, CD16b) and wildtype HNA-1 antigens associate with non-specific human IgG antibodies by its Fc binding domain. This non-specific binding between human IgG Fc and Fc gamma receptor type Mb interferes with the detection limits and sensitivity for HNA-1 specific antibodies. In particular, detection of HNA-1 specific antibodies using solid phased assays are hindered by the high background from the presence of non-HNA-1 specific human IgG in the tested samples.

Three binding domains of FcγRIIIb have been loosely defined and are denoted herein as Fc binding domain 1 (SEQ ID NO: 2) which spans residues 131 to 138 of SEQ ID NO: 1, Fc binding domain 2 (SEQ ID NO: 3) which spans residues 150 to 154 of SEQ ID NO: 1 and Fc binding domain 3 (SEQ ID NO: 4) which spans residues 175 to 181 of SEQ ID NO: 1. There are three Fc binding regions on the FcγRIIIb as determined by X-ray crystal structures of FcγRII, FcγRIII, and FcγRIIIb, and consensus alignment of all Fc gamma receptors (FcγRI, FcγRIIa, FcγRIIb, and FcγRIII) (The EMBO Journal 18(5):1095-1103, 1999; Immunity, 13:387-395, 2000; JBC 276(19):16469-16477, 2001). However, the exact amino acid sequences of the Fc binding mortif is disputed in the art.

Studies were carried out on the Fc domains to find the amino acids within the Fc domains that are essential for binding to the human IgG Fc. These studies involved modification of one or more sequential amino acid(s) in the Fc binding domains. Among them, SEQ ID NO: 5, SEQ ID NO: 29 and SEQ ID NO: 32 have been previously reported (J. Immunol. 152:4466-4474, 1994; JBC 271(7):3659-3666, 1996).

The invention provides for HNA-1 polypeptides in which the Fc binding domain has been modified. These modified polypeptides: (i) reduce the nonspecific antibody (IgG) binding to the Fc binding region, (ii) increase the sensitivity of antibodies specific for the HNA-1 antigen and (iii) increase the detectable range sensitivity these antibodies. The invention also provides for methods of using these modified HNA-1 polypeptides for the detection of HNA-1 specific antibodies and provides for methods of predicting whether a transfusion recipient has an increased risk for developing TRALI. The modified polypeptides of the invention have at least one amino acid substitution within an Fc binding domain of C gamma receptor type IIIb polypeptide (Uniprot Accession No. 075015; SEQ ID NO: 1) while maintaining a polymorphic structure typical of HNA-1 antigens.

The present invention also provides for the methods of detecting HNA-1 specific antibodies. HNA-1 specific antibodies include antibodies that specifically bind an any HNA-1 antigen including HNA-1a, HNA-1b and HNA-1c and these antibodies may bind one or more HNA-1 polymorph. HNA-1 polymorphic specific antibodies are antibodies that bind a particular HNA-1 polymoprph such as antibodies that specifically bind HNA-1a and no other HNA-1 antigens, or antibodies that specifically bind HNA-1b and no other HNA-1 antigens, or antibodies that specifically bind HNA-1c and no other HNA-1 antigens.

The HNA system comprises of five major different HNA antigens and the modified polypeptides of the invention which bind HNA-1 specific antibodies may be used in combination with wild-type and modified polypeptides which bind one or more HNA antigens, e.g. HNA-2, HNA-3a, HNA-3b, HNA-4a, HNA-5a and HNA-5b, to detect antibodies that bind antibodies that specifically bind members of the HNA system, The invention provides for kits for detecting antibodies specific for HNA-1 in combination with wild type polypeptides and modified polypeptides which bind one or more HNA antigens, e.g. HNA-2, HNA-3a, HNA-3b, HNA-4a, HNA-5a and HNA-5b to detect antibodies that bind antibodies that specifically bind members of the HNA system. HNA-1 specific antibodies and antibodies that detect other members of the HNA system (HNA-2, HNA-3a, HNA-3b, HNA-4a, HNA-4b, HNA-5a and HNA-5b) are detected using a flow cytometer or Luminex machines. Detection of the presence of any anti-HNA-1 specific antibody, or antibodies specific for any other member of the HNA system, provides a test to determine whether donor tissue intended for transplant or transfusion will induce TRALI or GVHD in a human recipient that expresses a different polymorphic HNA molecule.

For example, detection of any of HNA-1a, HNA-1b, and HNA-1c specific antibodies in donor tissue intended for transplants or transfusion is indicative of whether the donor tissue will induce TRALI or GVHD in a human recipient that expresses a different polymorphic HNA molecule.

The invention provides for methods of determining the susceptibility of a human transplant or transfusion recipient for developing TRALI or GVHD, wherein the donor tissue contains HNA-1 specific antibodies, comprising a) contacting a biological sample obtained from the human transplant or transfusion recipient prior to transplantation or transfusion with a panel presenting one or more HNA-1 antigens, such as of HNA-1a, HNA-1b and HNA-1c, and b) detecting binding of HNA-1 specific antibodies to the panel which is indicative of the presence of HNA-1 specific antibodies in the biological sample, and wherein the presence of HNA antibodies in the biological sample indicates that a human transfusion or transplant recipient is susceptible for developing TRALI or GVHD.

The panel of antibodies may be presented on a solid phased substrate. In one aspect of the invention, a mixture of microbeads coated with a panel of purified HNA antigens, HNA-1a, HNA-1b and HNA-1c, are used to determine the positive reaction patterns against the negative sera. The positive reaction is determined by the ratio (fold of increase) when compared to negative sera. The ratio for determining a positive reaction is carried out using the One Lambda Labscreen (Thermo Fisher Scientific) according to the manufacturer's instructions. The ratio can be found on the One Lambda LabScreen product inserts. NBG (Normalized BackGround) ratio was applied to determine the positive/negative reaction. The default cutoff for NBG ration is 2.2. The defined NBG ratio is based on the following equation: NBG ratio=(Sample-specific fluorescent value for bead #N/bead Sample-specific fluorescent value for Negative Control bead)/(Background NC Serum fluorescent value for bead #N/bead Background NC Serum fluorescent value for Negative Control bead).

The methods of the invention utilize microbeads coated with purified HNA-1 antigen for detecting anti-HNA-1 specific antibodies in human serum by flow cytometer or a Luminex analyzer. According to the methods of the invention, a panel of mixed microbeads coated with a panel of purified HNA-1 antigens is used. The invention also provides a panel microbeads coated with different purified HNA antigens, which are detectably distinguishable such as by being of different sizes (for flow cytometer) or having distinguishable labels (for Luminex analyzer).

For example, HNA antigens coated microbeads are incubated with a biological samples such as serum for a time sufficient to allow for binding, such as 30 minutes at room temperature. Serum dilution are determined by those of skill in the art but preferably in range from neat (no dilution) to a dilution of 1:10 in 1×PBS. Additional exemplary dilutions include 1:1, 1:2, 1:3, 1:4, 1:5, 1:6, 1:7, 1:8 and 1:9 in any acceptable solution. After incubation, the microbeads are then washed with wash buffer comprising PBS with 0.1% polysorbate 20 (TWEEN-20) three times. Subsequently, the microbeads are incubated with a labeled secondary antibody such as goat anti-Human IgG antibodies conjugated with Phycocrythrin (PE) or Fluorescent isothiocyanate (FITC) fluorescent labels and incubate for 20 minutes. The microbeads are then washed two times with wash buffer and analyzed on a flow cytometer or Luminex analyzer, depending on the type of microbeads used. A biological sample, e.g. sera, which contain anti-HNA-1 specific antibodies will show a fluorescent channel shift compared to negative sera. Signal thresholds can be established by testing both positive and negative control samples or by using mouse monoclonal antibodies specific to the HNA antigens. Using such a cut-off, anti-HNA positive serum will be assigned by a higher fluorescent channel shift than the threshold while negative anti-HLA sera will be assigned by a lower fluorescent channel shift than the threshold for flow cytometer. For the Luminex analyzer, the positive reaction patterns are determined by the ratio (fold of increase) when compared to negative sera or negative mouse monoclonal antibody. The appropriate signal threshold allows for a clear difference between positive and negative reactions.

The signal emitted by the selected portion of positive beads is statistically analyzed to determine the mean or median (or any other statistics such as peak, trimmed mean, trimmed peak etc.) intensity of the signal emitted by the detectable label. The portion of the subset of positive beads is preferably determined by the number of different probes and number of different labeled beads used in the screening assays. The positive beads are those that emit a signal that is greater than a selected threshold, wherein the threshold is indicative of the presence of one or more HNA-1 specific antibodies in the biological sample. Optionally, only a selected portion of positive reactive beads, e.g. those emitting the greatest signal intensity, are analyzed as described in US Publication No. 2009/0142762; incorporated by reference herein in its entirety. Exemplary software for analyzing the signal using a Flow cytometer is available from Luminex, Inc. (Austin, Tex.), Thermo Fisher Scientific and BD Biosciences (San Jose, Calif.). Additional software examples include WinMDI (Windows Multiple Document Interface for Flow Cytometry), FCS Express (De Novo Software, Thornhill, ON Canada), FlowJO (Tree Star, Inc.). The data may be analyzed using software that analyzes the intensity of detectable labels, which is standard in the art.

The selected threshold to determine positive beads (after the filtering step) will be the same for any single probe. The selected threshold is commonly determined by analyzing a panel of known positive samples and a panel of known negative samples, and identifying the differential between the two. A threshold is then set within that differential.

The methods of the invention may be carried out with microparticles, microbeads, beads or microsphere of any material, e.g. silica, gold, latex, polymers such as polystyrene, polysulfone and polyethyl, or hydrogel. Additional exemplary microbeadsare encoded with the dyes and the oligonucleotides are immobilized to the encoded microparticles, The microbeads used in the methods of the invention are commercially available from sources such from Luminex Inc., Invitrogen (Carlsbad, Calif.), Polysciences Inc. (Warrington, Pa.) and Bangs Laboratories (Fishers, Ind.) to name a few.

The microbeads of the invention may comprise a detectable label or another identifying characteristic. The microbeads may comprise a single fluorescent dye or multiple fluorescent dyes. In one embodiment, the microbeads are internally labeled with fluorescent dyes and contain surface carboxyl groups for covalent attachment of biomolecules. In another embodiment, the microbeads are internally labeled with fluorescent dyes and contain a surface layer of Avidin for near covalent binding of biotin and biotinylated ligands. In another embodiment, the microbeads may comprise a combination of different dyes, such as a fluorescent and a non-fluorescent dye. For example, the microbeads may be labeled with E)-5-[2-(methoxycarbonyl)ethenyl]cytidine, which is a nonfluorescent molecule, that when subjected to ultraviolet (UV) irradiation yields a single product, 3-β-D-ribofuranosyl-2,7-dioxopyrido[2,3-d]pyrimidine, which displays a strong fluorescence signal. In another embodiment, the microbeads may comprise bar codes as an identifiable characteristic as described in U.S. Patent Publication No. US 20070037195.

In another embodiment, the microbeads may be nanocrystals or quantum dots. These nanocrystals are substances that absorb photons of light, then re-emit photons at a different wavelength (fluorophores). In addition, additional florescent labels, or secondary antibodies may be conjugated to the nanocrystals. These nanocrystals are commercially available form sources such as Invitrogen, Thermo Fisher Scientific and Evident Technologies (Troy, N.Y.), The identifiable characteristic of the microparticle may be any nanoparticle DNA based detection methods or any nanoparticle protein based detection method. On example, is a bio bar code, which is an ultrasensitve method of detecting proteins using nanoparticle probes that are encoded with DNA that is unique to the protein target in the biological sample (Nam et al., Science 301, 1884-1886, 2003). Examples of nanoparticle DNA-based detection include colorimetric polynucleotide detection methods based on mercaptoalkyloligonucleotide-modified gold nanoparticles (Elghanian et al., Science 277, 1078-1080, 1997), chip-based detection methods that rely upon either light scattering or silver staining (Taton et al. Science 289, 1757-1760, 2000; Taton et al., J. Am. Chem. Soc., 123, 5164-5165, 2001) electrical detection method for DNA in which the target DNA is captured in the gap between two electrodes using a sandwich assay (Park et al., Science 295, 1503-1506, 2002) and DNA detection using chemoresponsive diffraction gratings interrogated simultaneously at multiple laser wavelengths (Cao et al., J. Am. Chem. Soc. 2003).

The invention can be carried out with any system that detects the identifiable characteristic or label, such as FLOW. Detection of fluorescent labels may also be carried out using a microscope or camera that will read the image on the microparticles, such as the Bioarray BeadChip (Bioarray Solutions, Ltd., Warren, N.J.). The BeadChip format combines microparticle ("bead") chemistry with semiconductor wafer processing in which binding to the microparticle is recorded using an optical microscope and camera.

Biological samples include whole blood, blood derivatives, red blood cell concentrates, plasma, serum, fresh frozen plasma, whole blood derived platelet concentrates, apheresis platelets, pooled platelets, intravenous gammaglobulin, cryoprecipitate, cebrospinal fluid, tissues and cells such as epithelial cells, such as those collected from the buccal cavity, stem cells, leukocytes, neutrophils and granulocytes. The biological samples may be obtained from a human donor of tissue or cells intended for transplantation or a human donor of blood or blood derivatives intended for transfusion. The biological sample may be obtained from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

Human Neutrophil Antigens

Human neutrophil antigens are also known as neutrophil-specific antigens or HNA. Currently there are 5 HNA antigen systems: HNA-1, HNA-2, HNA-3, HNA-4 and HNA-5. Alleles for HNA-1, 2, 3, 4 and 5 were identified and the corresponding glycoproteins were characterized (Stroncek, ASHI Quarterly 2004).

The HNA-1 has three major antigens: HNA-1a, HNA-1b, and HNA-1c. HNA-1 antigens belong to the low affinity Fc gamma receptor Mb (FcγRIIIb, CD16b). It is expressed on neutrophils only. The frequencies of the three major HNA-1 alleles vary depending on the racial groups. The HNA-1a differs from the HNA-1b by only four amino acids, at the amino acid locations of 36, 65, 82, and 108 (based on the Uniprot database access No: O75015). The glycosylation pattern between the HNA-1a and HNA-1b antigens are different because HNA-1b has six N-linked glycosylation sites while HNA-1a has only four glycosylation sites. The third major HNA-1 antigen, HNA-1c, is identical to HNA-1b except a single change of alanine to aspartate at the amino acid position 78. In additional to HNA-1a, HNA-1b and HNA-1c polymorphic structures, more HNA-1 polymorphisms have been identified in ethnic population. However, their nomenclatures are not well defined (Tissue Antigens 80:249-53 1-5, 2012).

The HNA-2 system has one well established antigen (HNA-2a, CD177). HNA-2a is only expressed on neutrophils and neutrophil precursors. There are polymorphic HNA-2 variants reported. However, most TRALI cases caused by HNA-2a are due to the lack of HNA-2a antigen on the neutrophil in transfusion recipients. Whether the polymorphic HNA-2 will contribute to TRALI or not is still unknown.

HNA-3a has been later identified as CTL2. It is a 706 amino acid membrane-spanning protein (about 80 kDa) that comprises 10 helical transmembrane domains. This protein is also known as SLC44A2, DKFZp666A071 2, F1144586 2 or PP1292. It is known to be involved in choline transport within the inner ear and is expressed on inner ear supporting cells. One report has been associated CTL-2 with Cochlin (J Assoc Res Otolaryngol. 8(4): 435-446, 2007). However, their functions are still unknown. The difference between HNA-3a and HNA-3b is due to a change of amino acid at position 154 from arginine to glutamine. 50% of HNA-3a associated TRALI cases were reported.

HNA-4 and HNA-5 are in the beta-integrin family. HNA-4 is expressed on granulocytes, monocytes and lymphocytes. The HNA-4a antigen was known as Mart or CD11b. The difference between HNA-4a and HNA-4b is a change of amino acid at position 61 from arginine to histidine. HNA-5a was previously known as Ond (CD11a), the αL integrin unit or leukocyte function antigen-1 (LFA-1). The difference between the HNA-5a and HNA-5b is due to change of amino acid at position 766 from Arginine to Threonine. (Stroncek, ASHI Quarterly 2004)

Human Leukocyte Antigens

An HLA class I molecule consists of a 45-kDa glycoprotein (heavy chain) non-covalently associated with a 12-kDa polypeptide, β2-microglobulin (β2 m). Association of β2 m with newly synthesized class I heavy chains is required in order for the HLA molecule to transport and present the peptide (Krangel et al., Cell 18: 979, 1979). However, β2 m free class I heavy chains were identified on activated T lymphocytes (Schnabl et al., J. Exp. Med. 171:1431, 1990) and other cell surfaces (Bix & Raulet, J. Exp. Med. 176(3) 829-34, 1992). Properly conformed β2 m free class I heavy chains were identified on the cells and were believed to have functional importance. β2 m can be dissociated from a HLA class I complex on a cell surface by acid treatment (Sugawara et al., J. Immunol. Methods, 100(1-2):83-90, 1987). β2 m can also be dissociated from HLA Class I complex coated on microbeads using the similar method of low pH treatment. (Pei et al. Visuals Clinical Histocompatability Workshop 2000, 9-10). Those β2 m-free HLA heavy chains are referred to as "denatured antigens." Antibodies against denatured class I HLA antigens have been detected in human sera from non-sensitized donors, however, they have not been well studied and currently the clinical significance of these antibodies is unclear.

HLA class II molecules are heterodimers formed by noncovalent linkage of two glycosylated polypeptide chains referred to as alpha and beta chains. The α subunit is 33 kDa and the β subunit is 28 kDa, and both chains are transmembrane polypeptides that have the same overall structure. The invariable a chain is encoded by the DRA HLA gene and this chain binds various β chains encoded by the DRB HLA genes. In addition, the DP and DQ HLA gene families each have one gene that encodes an α chain and a β chain. (Reviewed in Choo, Yonsei Med. J. 48: 11-23, 2007).

The HLA locus is highly polymorphic in nature. As disclosed in the Nomenclature for Factors of the HLA System 2000 (Hum. Immunol.; 62(4):419-68, 2001) there are 124 HLA-A alleles, 258 HLA-B alleles, 74 HLA-C alleles, 221 HLA-DRB1 alleles, 19 DRB3 alleles, 89 DRB4 alleles, 14 DRB5 alleles, 19 DQA1 alleles and 39 DQB1 alleles, with new alleles being discovered continuously. As testament to this rapid progress, a April 2007 update by the WHO nomenclature Committee for Factors of the HLA System (www.anthonynolan.com/HIG/) showed there are 545 HLA-A alleles, 895 HLA-B alleles, 307 HLA-C alleles, 8 HLA-E alleles, 12 HLA-H alleles, 9 HLA-J alleles, 6 HLA-K alleles, 4 HLA-L alleles, 4 HLA-P alleles, 3 HLA-V alleles, 3 DRA alleles, 494 DRB1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles.

Major-histocapatibility-complex class 1-related chain A (MICA) antigens are surface glycoproteins that are expressed on endothelial cells, dendritic cells, fibroblast, epithelial cells and many tumors. MICA antigens are not commonly expressed on lymphocytes, the cells typically used for cross-match analysis. Polymorphic MICA antigens are expressed on endothelial cells and have been found to be cytotoxic in the presence of serum complement, so it is likely that antibodies specific for MICA antigen are harmful for transplants. MICA antigens are also known s MIC-A, PERB11 and stress inducible class 1 homolog.

Fc Receptors

Fc receptors are polypeptide that bind to the Fc portion of the an immunoglobulin. Fc receptors which are specific to the Fc portion of IgG include FcγI (CD64), FCγRIIA (CD32), FCγRIIB (CD32), FcγIIIA (CD16a), FCγIIIB (CD16b) and FcRn. Fc receptors which are specific for IgE include FcεRI and FcεRII (CD23). FcαRI specifically bind the Fc portion of IgA. Fcα/μR specifically binds the Fc portion of IgA and IgM.

Method of Detecting HNA Specific Antibodies

The invention provides for methods of detecting HNA-1 specific antibodies in a biological sample. Methods of detecting of antibody include non-specific and specific assays such as, granulocyte immunofluorescence test, granulocyte immunofluorescence flow cytometry assay (GIFT-FC), monoclonal antibody immobilization of granulocyte antigens (MAIGA) assay, single radial immunodiffussion assay (SRID), enzyme immunoassay and hemagglutination inhibition assay (HAI).

An exemplary non-specific assay uses intact granulocytes as a target, e.g. GIFT-FC uses a panel of neutrophils with different HNAs (Davoren, et al. Transfusion 43(5): 641-5, 2003, Kobayashi et al, Ped. Res. 26: 246-249). The methods of the invention may be carried out with granulocytes transformed or transfected to express the modified polypeptides of the invention or antigenic fragments thereof. The neutrophils are first incubated with test sera followed by incubation with a fluorescently labeled secondary antibody, such as antihuman polyvalent immunoglobulin, IgG, IgM and IgA. After washing, the antibody binding to the cell suspensions is examined by flow cytometry.

An exemplary specific assay uses immobilized modified polypeptide of the invention as a target, e.g. MAIGA assay. MAIGA is an ELISA-based test that uses HNA-1 specific monoclonal antibodies to capture the neutrophil antigens within test sera. Subsequently, the cell mixtures are incubated with an enzyme labeled secondary antibody, such as anti-mouse IgG, and binding is detected with a colorimetric assay (Bux, et al. Transfusion Med. 3(2): 157-62, 1993, Metcalfe & Waters, Transfusion Med. 2:283-287, 1992.)

ELISA assay is used to determine total antibodies in the sample. The immunogen, e.g. the modified polypeptides of the invention or antigenic fragments thereof, is adsorbed to the surface of a microtiter plate. The test serum is exposed to the plate followed by an enzyme linked immunoglobulin, such as IgG. The enzyme activity adherent to the plate is quantified by any convenient means such as spectrophotometers and is proportional to the concentration of antibody directed against the immunogen present in the test sample. In addition, modified polypeptides of the invention or antigenic fragments thereof may be attached to solid substrates such as membranes, beads, filters, glass, silicon, metal, metal-alloy, anopore, polymeric, nylon or plastic for detection of HNA-1 specific antibodies.

The SRID assay utilizes a layer of a gel, such as agarose, containing the antigen being tested. A well is cut in the gel and the test sera are placed in the well. Diffusion of the antibody out into the gel leads to the formation of a precipitation ring whose area is proportional to the concentration of the antibody in the serum being tested.

HAI utilizes the capability of an immunogen to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen.

Additional assays to detect circulating anti-HNA-1 specific antibodies in the serum of the transplant or transfusion patient may be used. In such an assay, serum is screened for the presence of anti-HNA-1 specific antibodies through detection of complement-mediated lytic activity. Serum is screened for complement-mediated lytic activity against T and B lymphocytes from a panel of individuals representing the most frequently encountered HNA-1 antigens. The assay is performed in the presence or absence of dithioerythritol.

The methods of detecting an HNA-1 specific antibodies may also be carried out with neutrophils or any cell type transformed or transfected to express the modified polypeptides of the invention or antigenic fragments thereof. The methods may be carried out will cells that do not endogenously express HNA-1, such as B-cells, CHO cells or insect cells.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., Virology, 52:456 (1973); Sambrook et al., Molecular Cloning, a laboratory Manual, Cold Spring Harbor Laboratories (New York, 1989); Davis et al., Basic Methods in Molecular Biology, Elsevier, 1986; and Chu et al., Gene, 13:197 (1981). Such techniques can be used to introduce one or more of the modified polypeptides of the invention into suitable host cells.

The term "transformation" as used herein refers to a change in a cell's genetic characteristics, and a cell has been transformed when it has been modified to contain a new DNA. For example, a cell is transformed where it is genetically modified from its native or wild type state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Exemplary B cell that may be used in the methods of the invention include EB-3 cells (ATCC CCL85), K-562 cells (ATCC CCL243), RAJI cells (ATCC CCL86), Jiyoye cells (CCL87), IM-9 (ATCC159), Daudi cells (ATCC CCL213), NC-37 cells (ATCC 214), Mo-B cells (ATCC 245), KG-1 cells (ATCC CCL246), H2126 cells (ATCC 256), BL2126 cells (ATCC 256) and MCL-5 cells (ATCC CCL10575). Other exemplary cells that may be used in the methods of the invention include Chinese hamster ovary cells (CHO) (ATCC No. CCL61), CHO DHFR-cells (Urlaub et al., Proc. Natl. Acad. Sci. USA, 97:4216-4220 (1980)), human embryonic kidney (HEK) 293 or 293T cells (ATCC No. CRL1573), or 3T3 cells (ATCC No. CCL92), monkey COS-1 (ATCC No. CRL1650) and COS-7 cell (ATCC No. CRL1651), and CV-1 cells (ATCC No. CCL70). In addition, insect cells may be used in the methods of the invention such as SF-9 and HIS cells.

The invention also provides for methods of detecting HNA-1 specific antibodies within a biological sample by contacting a biological sample with an aptamer that mimics a antigenic fragment or epitope of a modified polypeptide of the invention. Aptamers are macromolecules comprising single stranded oligonucleotides that have a sequence-dependent three-dimensional shape that will bind a target protein with high affinity and specificity. The invention contemplates developing and using aptamers that have a sequence that mimics the HNA-1 epitope and therefore binds to HNA-1 specific antibodies. These aptamers may be used in any of the methods of the invention to detect the presence of HNA-1 specific antibodies.

The aptamers of the invention may comprise single stranded RNA or DNA oligonucleotides ranging in size between 15 and 50 bases that are fused to a scaffold such as thioredoxin. The aptamers will mimic the physical or structural characteristics of the HNA-3a and HNA-3b peptides of the invention. The aptamers are generally derived from combinatorial libraries through an in vitro selection process known as Systematic Evolution of Ligands through Exponential enrichment (SELEX). Exemplary methods for identifying and synthesizing aptamers against HNA-3a or HNA-3b antibodies are presented in Lo, Antibody Engineering: methods and protocols Vol 248 of Methods in Molecular Biology, Humana Press 2004, Klussmann, The Aptamer Handbook: functional oligonucleotides and their applications Wily-VCH, 2006, and Jayasena Clin. Chem. 45:168-1650, 1999. Any of the assays described herein may be used to confirm that the contemplated aptamers bind to HNA-3a or HNA-3b specific antibodies.

Furthermore, the invention provides for methods of detecting HNA-1 specific antibodies using peptides that mimic the secondary or tertiary structure of the antigenic fragments of the modified polypeptides of the invention, while differing in primary amino acid structure. The structural characteristics of these peptides cause the HNA-1 specific antibodies to cross react with these peptides. These peptides may be identified using standard methods in the art such as phage display peptide libraries and combinatorial libraries.

Methods of Distinguishing HNA-1 Specific Antibodies

Any of the techniques described herein to detect HNA-1 specific antibodies in a biological sample also may be used to distinguish if a particular antibody specifically binds to HNA-1. The assays would be carried out with the full length modifiedpolypeptide of the invention or antigenic fragments thereof. In particular, the peptides used in these assays may retain any secondary or tertiary structure that will distinguish the HNA-1 epitope. Furthermore, assays using cells transformed or transfected to express HNA-1 may be used to identify and distinguish HNA-1 specific antibodies.

Polynucleotides and Recombinant Expression of Modified Polypeptides

The modified polypeptides of the invention may comprise one or more additional conservative amino acid substitutions that do not affect the biological and/or immunogenic activity of the polypeptide. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "ala-nine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine. General rules for amino acid substitutions are set forth in Table 1 below.

Conservative Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The modified polypeptides of the invention may be encoded by nucleotide sequences that are substantially equivalent to the polynucleotides encoding the polypeptides of the invention. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the polynucleotide sequences encoding the modified polypeptide amino acid sequences of the invention.

Included within the scope of the nucleic acid sequences of the invention are nucleic acid sequence fragments that hybridize under stringent conditions to the nucleotide sequences encoding the modified polypeptides of the invention, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015M sodium citrate at 65-68° C. or 0.015 M sodium chloride, 0.0015M sodium citrate, and 50% formamide at 42° C. See Sambrook et al., Molecular Cloning: A Laboratory Manual, 2.sup.nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6x.SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4 (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

The sequences falling within the scope of the present invention are not limited to these specific sequences, but also include allelic and species variations thereof. Preferred computer program methods to determine identity and similarity between two sequences include, but are not limited to, the GCG program package, including GAP (Devereux et al., Nucl. Acid. Res., 12:387-1984; Genetics Computer Group, University of Wisconsin, Madison, Wis.), BLASTP, BLASTN, and FASTA (Altschul et al., J. Mol. Biol., 215: 403-410, 1990). The BLASTX program is publicly available from the National Center for Biotechnology Information (NCBI) and other sources (BLAST Manual, Altschul et al. NCB/NILM/NIH Bethesda, Md. 20894; Altschul et al., supra). The well known Smith Waterman algorithm may also be used to determine identity.

The terms "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

The invention provides for transforming or transfecting host cells with a nucleic acid encoding the amino acid sequence of a modified polypeptide of the invention. A nucleic acid molecule encoding the amino acid sequence of a modified HNA-1 polypeptide may be inserted into an appropriate expression vector using standard ligation techniques. Exemplary vectors include bacterial vectors, eukaryotic vectors, plasmids, cosmids, viral vectors, adenovirus vectors and adenovirus associated vectors.

The expression vectors preferably may contain sequences for cloning and expression of exogenous nucleotide sequences. Such sequences may include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

The vector may contain a sequence encoding a "tag" or exogenous amino acid sequence, such as an oligonucleotide molecule located at the 5' or 3' end of the modified polypeptide coding sequence; an oligonucleotide sequence encoding polyHis (such as hexaHis), FLAG, hemaglutinin influenza virus (HA), V5 or myc or other tags, for which commercially available antibodies exist. This tag may be fused to the modified polypeptide upon expression. A selectable marker gene element encoding a protein necessary for the survival and growth of a host cell grown in a selective culture medium may also be a component of the expression vector. Exemplary selection marker genes include those that encode proteins that complement auxotrophic deficiencies of the cell; or supply critical nutrients not available from complex media. The invention also contemplates that the modified polypeptides of the inventions comprises one or more of these exogenous amino acid sequence.

A leader, or signal, sequence may be used to direct the modified polypeptide out of the stem cell after administration. For example, a nucleotide sequence encoding the signal sequence is positioned in the coding region of the modified polypeptide nucleic acid, or directly at the 5' end of the modified polypeptide coding region. The signal sequence may be homologous or heterologous to the modified polypeptide gene or cDNA, or chemically synthesized. The secretion of the modified polypeptide from the stem cell via the presence of a signal peptide may result in the removal of the signal peptide from the secreted modified polypeptide. The signal sequence may be a component of the vector, or it may be a part of the nucleic acid molecule encoding the modified polypeptide that is inserted into the vector.

The expression vectors used in the methods of the invention may contain a promoter that is recognized by the host organism and operably linked to the nucleic acid sequence encoding the modified polypeptide. Promoters are untranscribed sequences located upstream to the start codon of a structural gene that control the transcription of the structural gene. Inducible promoters initiate increased levels of transcription from DNA under their control in response to some change in culture conditions, such as the presence or absence of a nutrient or a change in temperature. Alternatively, constitutive promoters initiate continual gene product production with little or no control over gene expression. A large number of promoters, recognized by a variety of potential host cells, are well known. A suitable promoter is operably linked to the nucleic acid molecule encoding the modified polypeptide. The native HNA-1 gene promoter sequence may be used to direct amplification and/or expression of the modified polypeptide nucleic acid molecule. A heterologous promoter also may be used to induce greater transcription and higher yields of the modified polypeptide expression as compared to the modified polypeptide expression induced by the native promoter.

In addition, an enhancer sequence may be inserted into the vector to increase the transcription of a DNA encoding the modified polypeptide. Enhancers are cis-acting elements of DNA, usually about 10-300 bp in length, that act on the promoter to increase transcription. Enhancer sequences available from mammalian genes include globin, elastase, albumin, alpha-feto-protein and insulin. Exemplary viral enhancers that activate eukaryotic promoters include the SV40 enhancer, the cytomegalovirus early promoter enhancer, the polyoma enhancer, and adenovirus enhancers. While an enhancer may be spliced into the vector at a position 5' or 3' to a nucleic acid molecule encoding the modified polypeptide, it is typically located at a site 5' from the promoter.

The transformation of an expression vector encoding a modified polypeptide into a host cell may be accomplished by well-known methods such as transfection, infection, calcium chloride, electroporation, microinjection, lipofection or the DEAE-dextran method or any other technique known in the art. These methods and other suitable methods are well known in the art, for example, in Sambrook, Molecular Cloning: A Laboratory Manual, Cold Spring Harbor Laboratory Press; 3rd ed., 2001.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15 □ (Novagen, Madison, Wis.), pGEX (Pharmacia Biotech, Piscataway, N.J.), pEGFP-N2 (Clontech, Palo Alto, Calif.), pETL (Blue-BacII; Invitrogen), pDSR-alpha (PCT Publication No. WO90/14363) and pFastBacDual (Gibco/BRL, Grand Island, N.Y.).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.). The recombinant molecules can be introduced into host cells via transformation, transfection, infection, or other known techniques.

Host cells may be prokaryotic host cells (such as *E. coli*) or eukaryotic host cells (such as a yeast cell, an insect cell or a vertebrate cell). The host cell, when cultured under appropriate conditions, synthesizes a modified polypeptide of the invention which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5a, DH10, and MC1061 (ATCC No. 53338)) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces* cerivisae and *Pichia pastoris*.

Additionally, where desired, insect cell systems may be utilized in the methods of the present invention. Such systems are described for example in Kitts et al., Biotechniques, 14:810-817 (1993); Lucklow, Curr. Opin. Biotechnol., 4:564-572 (1993); and Lucklow et al. (J. Virol., 67:4566-4579 (1993). Preferred insect cells are Sf-9 and Hi5 (Invitrogen, Carlsbad, Calif.).

Kits

The invention provides for kits to carry out any of the methods of the invention. Kits according to the invention comprises components for detecting HNA-1 specific antibodies in a biological sample. The kit can comprise an isolated or recombinant wild type and modified HNA-1 polypeptide or an antigenic fragment thereof that forms a complex with HNA-1 specific antibodies in a biological sample and a known HNA-1 specific antibody for a positive control. The invention further provides for kits for detecting antibodies specific for other HNA specific antibodies such as HNA-2, HNA-3a, HNA-3b, HNA-4a, HNA-4b and/or HNA-5a, HNA-5b in addition to antibodies specific for HNA-1. These kits will comprise CD177 or antigenic fragments thereof for detection of HNA-2 and known antibodies that are specific for HNA-2. The kits will comprise of full length CTL-2 molecules for HNA-3a detection. The kits will comprise CD11b (CR3) or antigenic fragments thereof for HNA-4a detection and CD11a (LFA-1) or antigenic fragments thereof for detection of HNA-5a and known antibodies that are specific for HNA-4a and HNA-5a. Furthermore, the invention provides for kits for detecting antibodies specific for HLA in a biological sample in addition to antibodies specific for HNA, which will contain polypeptides containing the HLA antigen and known antibodies that are specific for HLA.

Kits useful for detecting antibodies specific for HLA-1 and optionally antibodies specific for other HNA and/or HLA antigens may further comprise any components necessary to carry out the detection assays that are conventional in the art. For example, the kits may comprise the components necessary to carry out SRID, ELISA, HAI, MAIGA assay, GIIFT, MLAT, and GAT.

Other aspects and advantages of the present invention will be understood upon consideration of the following illustrative example.

EXAMPLES

The present invention is illustrated by the following examples that are not intended to limit the invention. Example 1 describes experiments demonstrating the use of modified HNA-1a polypeptides that have increased sensitivity for anti-HNA-1a specific antibodies. Example 2 describes experiments demonstrating the use of modified HNA-1b polypeptides that have increased sensitivity for anti-HNA-1b specific antibodies. Example 3 describes experiments demonstrating the use of modified HNA-1c polypeptides that have increased sensitivity for anti-HNA-1c specific antibodies. Example 4 describes detection ratios for anti-HNA-2 specific antibodies. Example 6 describes detection ratios for anti-HNA-3a and HNA-3b specific antibodies. Example 7 describes detection ratios for anti-HNA-4a specific antibodies. Example 8 describes detection ratios for anti-HNA-5a specific antibodies.

Example 1

Increased Sensitivity for Anti-HNA-1a Specific Antibodies

The sensitivity of the modified HNA-1a proteins for anti-polymophic HNA-1a antibodies was tested. Wild type and modified HNA-1a proteins were coated on microbeads. The modified HNA-1a proteins had the L136A substitution (SEQ ID NO: 15), K138T substitution (SEQ ID NO. 19), and the W131F substitution (SEQ ID NO: 5). The negative sera (#LSNC) was as defined the human sera that does not have positive reaction against any HLA or HNA proteins and the HNA-1a positive sera was affirmed by neutrophil agglutination assay.

HNA-1a proteins were incubated with serum known to be positive for anti-HNA-1a antibodies and serum known to be negative for anti-HNA-1a antibodies for 30 minutes. Positive sera were diluted from 1:5 to 1:25 while negative sera was neat. The microbeads were subsequently washed with wash buffer comprising PBS with 0.1% polysorbate 20 (TWEEN) and incubated with goat anti-human IgG antibodies conjugated with phycocrythrin (PE) for 30 minutes. The microbeads were washed two times with wash buffer and analyzed on a Luminex analyzer according to the manufacturer's instructions.

The reaction patterns were compared. The positive reaction patterns were determined by the ratio (fold of increase) when compared to negative sera. The proper threshold was established to define a clean cut-off between the positive and negative reactions. Fold of increase against the negative sera was used to determine the sensitivity of the wild type HNA-1a v.s. modified HNA-1a polypeptides (Table 1; based on 10 tests).

Figure 2:
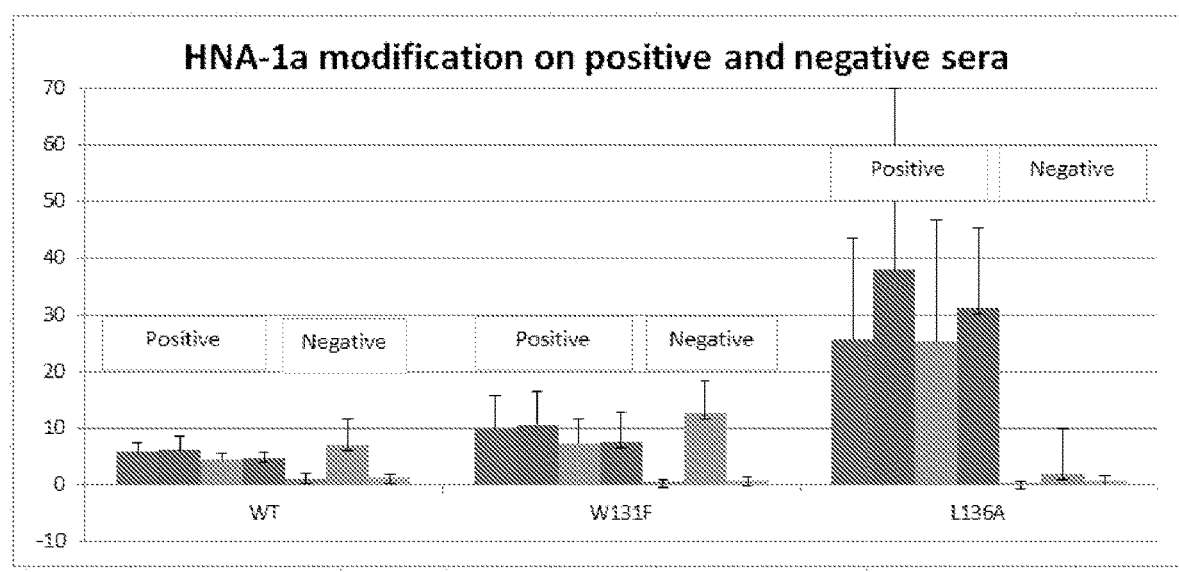
FIG. 2 summarizes the improvement of detection sensitivity for HNA-1 specific antibodies by HNA-1a modified polypeptides having the W131F or the L136A compared to wild-type HNA-1a polypeptide.

For the wild type HNA-1a proteins, about 6 to 13 fold increase in reactivity with the positive sera was observed when compared to the reactivity of the wild type HNA-1 proteins to the negative sera. Modification of HNA-1a polypeptides in their Fc binding domains either in W131F, L136A, or K148T locations decrease the background signals value from about 1900 of wild type to 300~500 MFI. For the HNA-1a modified polypeptide with the W131F substitution, there was an unexpected increase in the reactivity with 1 of the 3 negative sera tested. The modified W131F reactivity to this negative sera increased 7 fold while the reactivity of the wild type the negative sera increased 13 fold. For the HNA-1a modified protein having the L136A substitution, there was about 23 to 33 fold increase in reactivity with the positive sera when compared to the reactivity of the wild type HNA-1 antigens to the negative sera. This clearly shows the modified HNA-1a polypeptide having the L136A substitution increased the sensitivity for anti-polymorphic specific HNA-1a antibody detection while avoid the potential fold of increased reactivity for the negative sera. Data from an additional study demonstrating improvement in detection sensitivity between wild type HNA-1a polypeptide and modified HNA-1a polypeptide having the polypeptides substitution is provided in FIG. 1. The results are summarized in FIG. 2 based on eight tests.

TABLE 1

The reaction ratio of HNA-1a WT v.s. HNA-1a modified proteins

|  | HNA1a WT | HNA-1a W131F modified | HNA-1a L136A modified | HNA-1a K138T modified |
|---|---|---|---|---|
| Fold Increased Ratio Against Negative Sera | | | | |
| Negative Sera (#LSNC) | 1 | 1 | 1 | 1 |
| Positive Sera (#14) | 8 ± 1 | 10 ± 2 | 23 ± 7 | 13 ± 3 |
| Positive Sera (#Suarez) | 13 ± 3 | 9 ± 1 | 33 ± 10 | 11 ± 2 |
| Positive Sera (#Comartin) | 6 ± 1 | 7 ± 1 | 26 ± 7 | 8 ± 3 |
| Background Value (MFI) | | | | |
| Negative Sera (#LSNC) | 1908 ± 825 | 417 ± 130 | 290 ± 74 | 450 ± 157 |

Example 2

Increased Sensitivity For Anti-HNA-1b Specific Antibodies

The sensitivity of the modified HNA-1b proteins for anti-polymophic specific HNA-1b antibodies was tested as described in Example 1. The modified HNA-1b proteins had the L136A substitution (SEQ ID NO: 15), K138T substitution (SEQ ID NO. 19), and the W131F substitution (SEQ ID NO:5). The reaction patterns were compared. Fold of increase against the negative sera was used to determine the sensitivity of the wild type HNA-1b v.s. modified HNA-1b. (Table 2; based on 11 tests).

Modification of HNA-1b polypeptides in their Fc binding domains, either in W131F, L136A, or K148T locations, decrease the non-specific background signal value from about 1900 of wild type to less than 300 MFI. For the wild type HNA-1b proteins, about 6 to 13 fold increase in reactivity with the positive sera was observed when compared to the reactivity of the wild type HNA-1 proteins to the negative sera. For the HNA-1b modified protein having the W131F substitution, there was a 9 to 19 fold increase in reactivity with 3 positive sera. Although the fold of increase also observed in the negative sera tested, the increase is not significant. For the modified HNA-1b modified polypeptide having the L136A substitution, about 8 to 23 fold increase in reactivity with the positive sera was observed when compared to the reactivity of the wild type HNA-1b antigens to the negative sera. This clearly shows the modified HNA-1b polypeptide having the L136A substitution increased the sensitivity for anti-polymorphic specific HNA-1b antibody detection.

Figure 3:
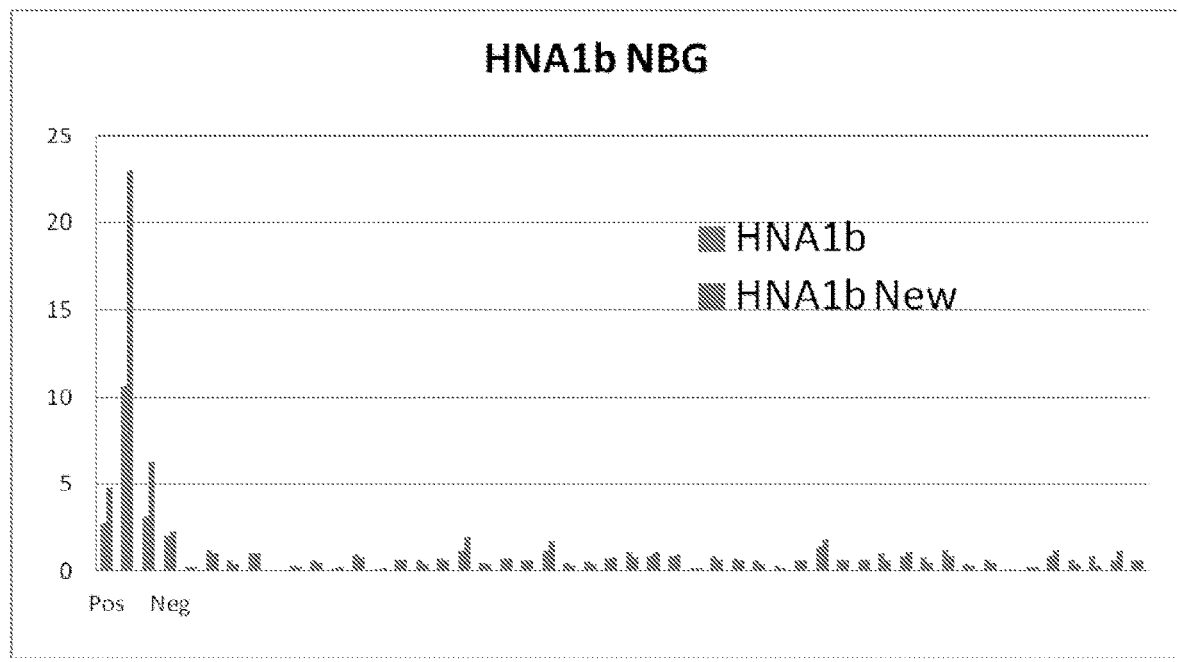
FIG. 3 depicts the improvement of detection sensitivity for HNA-1 specific antibodies by HNA-1b modified polypeptides having the L136A substitution compared to wild-type HNA-1b polypeptide.
Figure 4:
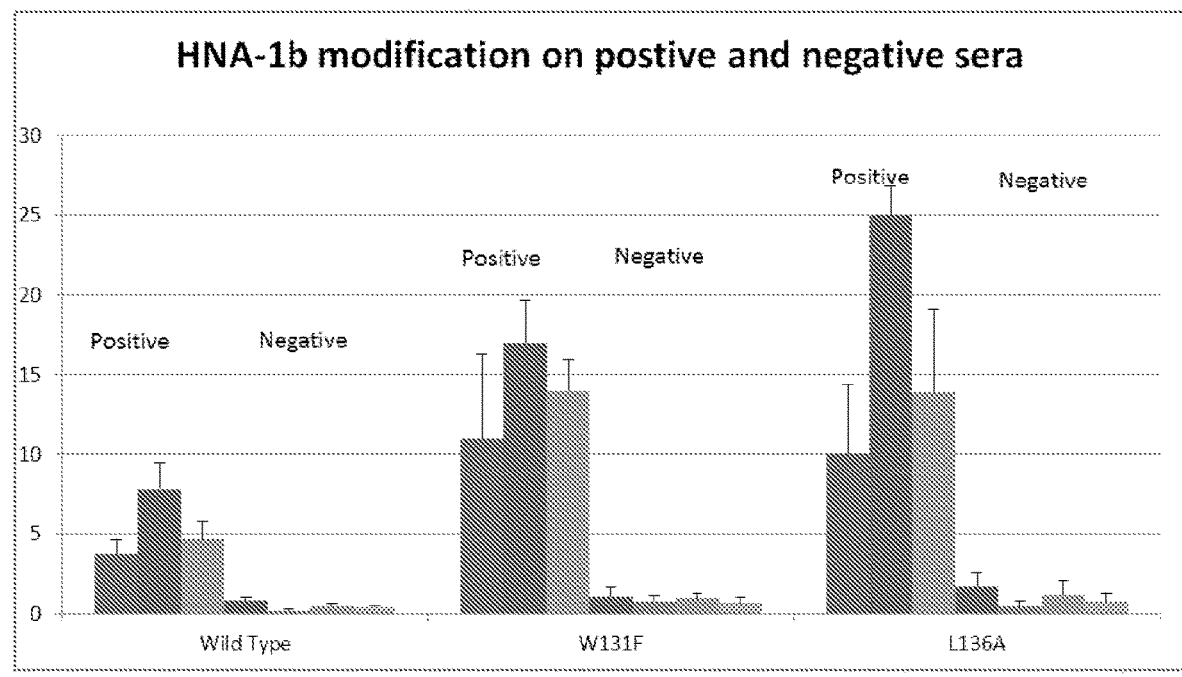
FIG. 4 summarizes the improvement of detection sensitivity for HNA-1 specific antibodies by HNA-1b modified polypeptides having the W131F or the L136A compared to wild-type HNA-1b polypeptide.

Data from an additional study demonstrating the improvement in detection sensitivity between wild type HNA-1b polypeptide and modified HNA-1b polypeptide having the L136A substitution is provided in FIG. 3. The results are summarized in FIG. 4 based on 12 tests.

TABLE 2

The reaction ratio of HNA-1b WT v.s. HNA-1b modified proteins

|  | HNA-1b WT | HNA-1b W131F modified | HNA-1b L136A modified | HNA-1b K138T modified |
|---|---|---|---|---|
| Fold Increased Ratio Against Negative Sera | | | | |
| Negative Sera (#LSNC) | 1 | 1 | 1 | 1 |
| Positive Sera (#15) | 11 ± 2 | 9 ± 4 | 8 ± 1 | 7 ± 1 |
| Positive Sera (#24) | 6 ± 2 | 19 ± 2 | 23 ± 3 | 18 ± 8 |
| Positive Sera (#Sink) | 13 ± 2 | 13 ± 4 | 12 ± 2 | 13 ± 3 |
| Background Value (MFI) | | | | |
| Negative Sera (#LSNC) | 1971 ± 416 | 183 ± 38 | 277 ± 53 | 187 ± 50 |

Example 3

Increased Sensitivity For Anti-HNA-1c Specific Antibodies

The sensitivity of the modified HNA-1c proteins for anti-polymophic specific HNA-1c antibodies was tested as described in Example 1. The modified HNA-1c proteins had the L136A substitution (SEQ ID NO: 15), K138T substitution (SEQ ID NO: 19), and W131F substitution (SEQ ID NO: 5). The reaction patterns were compared. Fold of increase against the negative sera was used to determine the sensitivity of the wild type HNA-1c v.s. modified HNA-1c. (Table 3; based on 9 tests).

Figure 5:
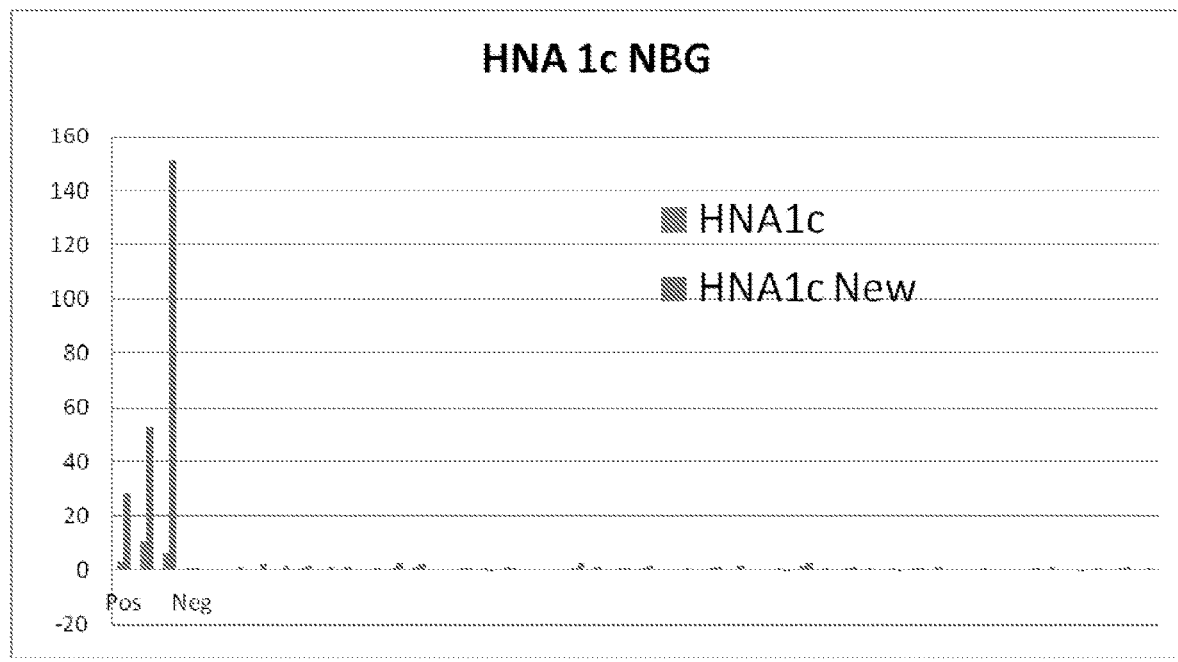
FIG. 5 depicts the improvement of detection sensitivity for HNA-1 specific antibodies by HNA-1c modified polypeptides having the W131F substitution compared to wild-type HNA-1a polypeptide.

Modification of HNA-1c polypeptides in their Fc binding domains either in W131F, L136A, or K148T locations decrease the non-specific background signal value from about 1500 of wild type to less than 210 MFI. For the wild type HNA-1c proteins, about 3 to 20 fold increase in reactivity with the positive sera was observed when compared to the reactivity of the wild type HNA-1c proteins to the negative sera. For the modified HNA-1c polypeptide having the W131F substitution, about 16 to 94 fold increase in reactivity with the positive sera was observed when compared to the reactivity of the wild type HNA-1 antigens to the negative sera. This clearly shows the modified HNA-1c polypeptide having the W131F substitution increased the sensitivity for anti-polymorphic specific HNA-1c antibody detection. The improvement in detection sensitivity between wild type HNA-1c polypeptide and modified HNA-1c polypeptide having the W131F substitution is provided in FIG. 5

Example 4

Detection Ratios For Anti-HNA-2 Specific Antibodies

Figure 6:
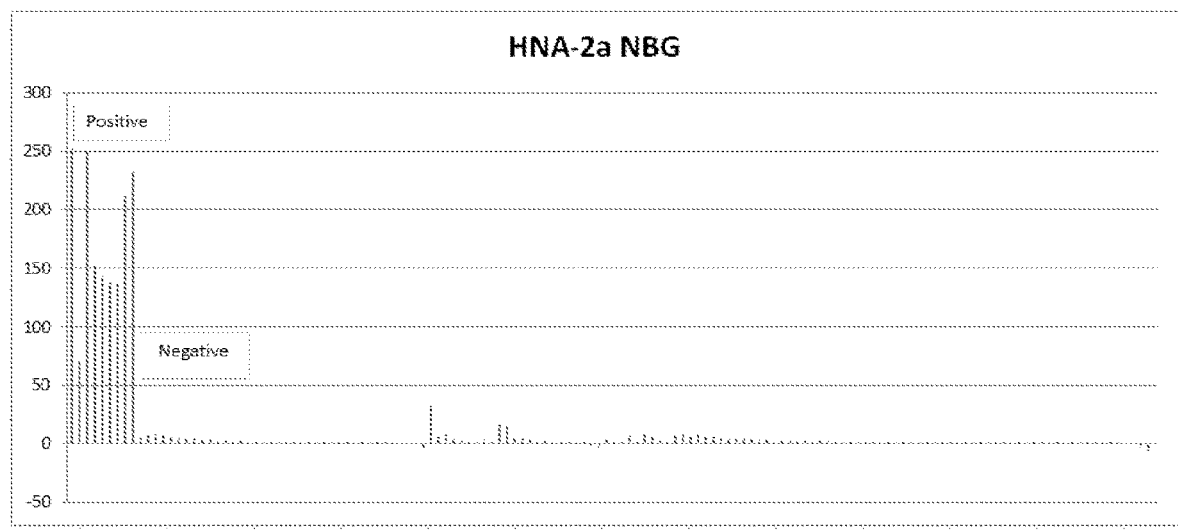
FIG. 6 depicts the detection sensitivity for HNA-2 specific antibodies.

The detection ratio for HNA-2 was examined using purified full length HNA-2 proteins. The wild type proteins were coated on microbeads. The negative sera (#LSNC) was defined as the human sera that does not have positive reaction against any HLA or HNA proteins and the HNA-2 positive sera was affirmed by neutralphil agglutination assay. The microbeads were incubated with the sera and analyzed as described in Example 1. The reaction pattern were compared and provided in Table 4 (based on 7 tests). The difference in detection sensitivity between HNA-3a positive sera and negative sera is provided in FIG. 6.

TABLE 4

The detection ratio of HNA-2 molecules with HNA-2 positive and HNA-2 negative sera

|  | Purified HNA-2 protein |
|---|---|
| Negative Sera (#LSNC) | 1 |
| Positive Sera (#Bladyka) | 89 ± 44 |
| Positive Sera (#Bagbee) | 99 ± 56 |
| Positive Sera (#Ball) | 167 ± 81 |
| Positive Sera (#23) | 153 ± 75 |
| Positive Sera (#A2407) | 94 ± 47 |

TABLE 3

The reaction ratio of HNA-1c WT v.s. HNA-1c W131F modified protein

|  | HNA-1c WT | HNA-1c W131F modified | HNA-1c L136A modified | HNA-1c K138T modified |
|---|---|---|---|---|
| Fold Increased Ratio Against Negative Sera | | | | |
| Negative Sera (#LSNC) | 1 | 1 | 1 | 1 |
| Positive Sera (#Forgaty) | 20 ± 9 | 94 ± 15 | 15 ± 10 | 19 ± 18 |
| Positive Sera (#15) | 3 ± 1 | 16 ± 4 | 6 ± 2 | 3 ± 1 |
| Positive Sera (#24) | 19 ± 6 | 21 ± 2 | 22 ± 8 | 17 ± 4 |
| Positive Sera (#Sink) | 12 ± 4 | 72 ± 10 | 10 ± 4 | 16 ± 9 |
| Background Value (MFI) | | | | |
| Negative Sera (#LSNC) | 1500 ± 339 | 181 ± 31 | 209 ± 108 | 126 ± 55 |

Example 5

Detection Ratios For Anti-HNA-3a and HNA-3b Specific Antibodies

Figure 7:
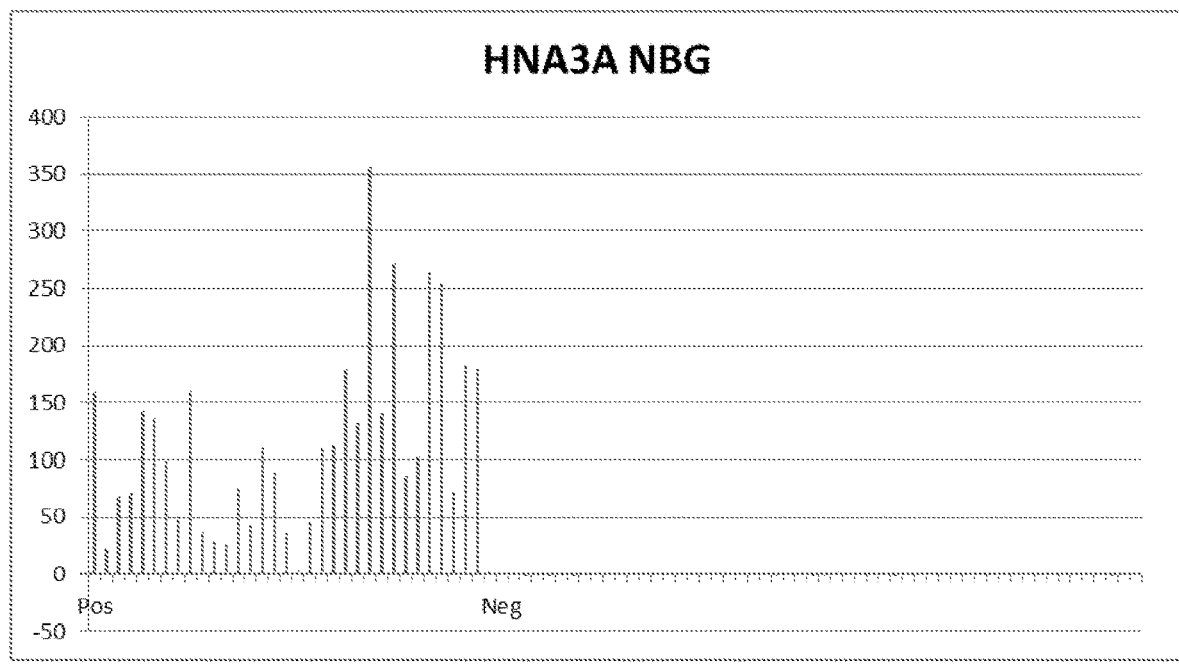
FIG. 7 depicts the detection sensitivity for HNA-3a and HNA-3b specific antibodies.

The detection ratio for HNA-3a was examined using purified full length HNA-3a and HNA-3b proteins. The wild type proteins were coated on microbeads. The negative sera (#LSNC) was defined as the human sera that does not have positive reaction against any HLA or HNA proteins, and the HNA-3 positive sera was affirmed by neutralphil agglutination assay. The microbeads were incubated with the sera and analyzed as described in Example 1. The reaction pattern were compared and provided in Table 5 (based on 11 tests). The difference in detection sensitivity between HNA-3a positive sera and negative sera is provided in FIG. 7.

TABLE 5

The detection ratio of HNA-3a molecules with HNA-3a positive and HNA-3a negative sera

|  | Purified HNA-3a protein |
| --- | --- |
| Negative Sera (#LSNC) | 1 |
| Positive Sera (#292092) | 216 ± 93 |
| Positive Sera (#HGW512) | 95 ± 46 |
| Positive Sera (#TRC11) | 53 ± 26 |

Example 6

Detection Ratios For Anti-HNA-4a Specific Antibodies

Figure 8:
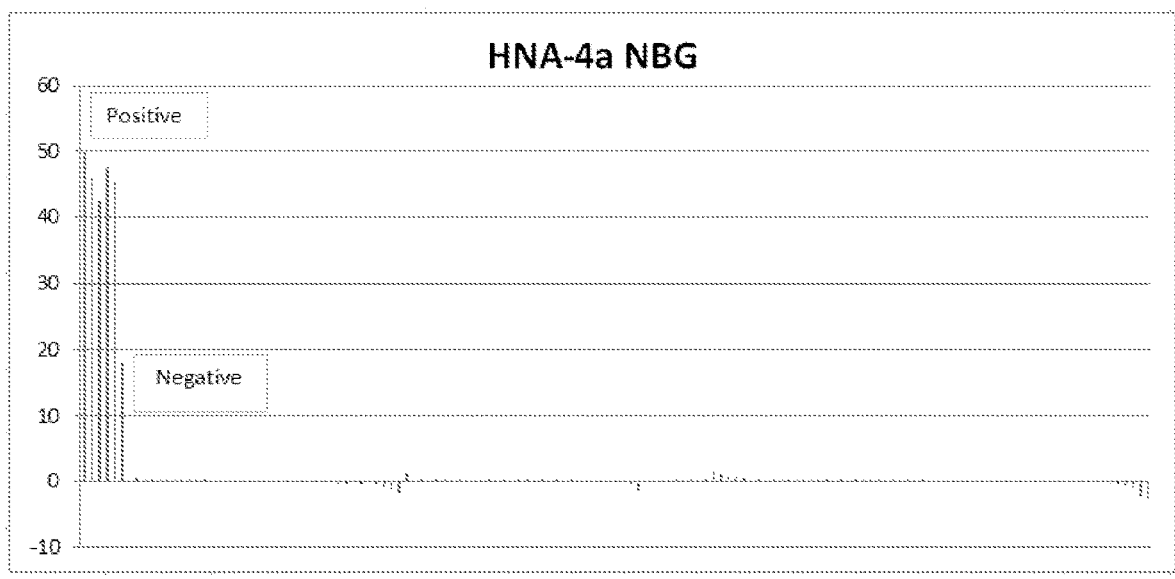
FIG. 8 depicts the detection sensitivity for HNA-4a specific antibodies.

The detection ratio for HNA-4a was examined using purified full length HNA-4a proteins. The wild type proteins were coated on microbeads. The negative sera (#LSNC) was defined as the human sera that does not have positive reaction against any HLA or HNA proteins and the HNA-4a positive sera was affirmed by neutralphil agglutination assay. The microbeads were incubated with the sera and analyzed as described in Example 1. The reaction pattern were compared and provided in Table 5 (based on 6 tests). The difference in detection sensitivity between HNA-3a positive sera and negative sera is provided in FIG. 8.

TABLE 6

The detection ratio of HNA-4a molecules with HNA-4a positive and HNA-4 negative sera

|  | Purified HNA-4a protein |
| --- | --- |
| Negative mouse IgG | 1 |
| Positive mouse IgG (#ICRF44) | 594 ± 185 |
| Positive mouse IgG (#HB249) | 592 ± 158 |
| Positive mouse IgG (#TS1/18) | 543 ± 213 |

Example 7

Detection Ratios For Anti-HNA-5a Specific Antibodies

Figure 9:
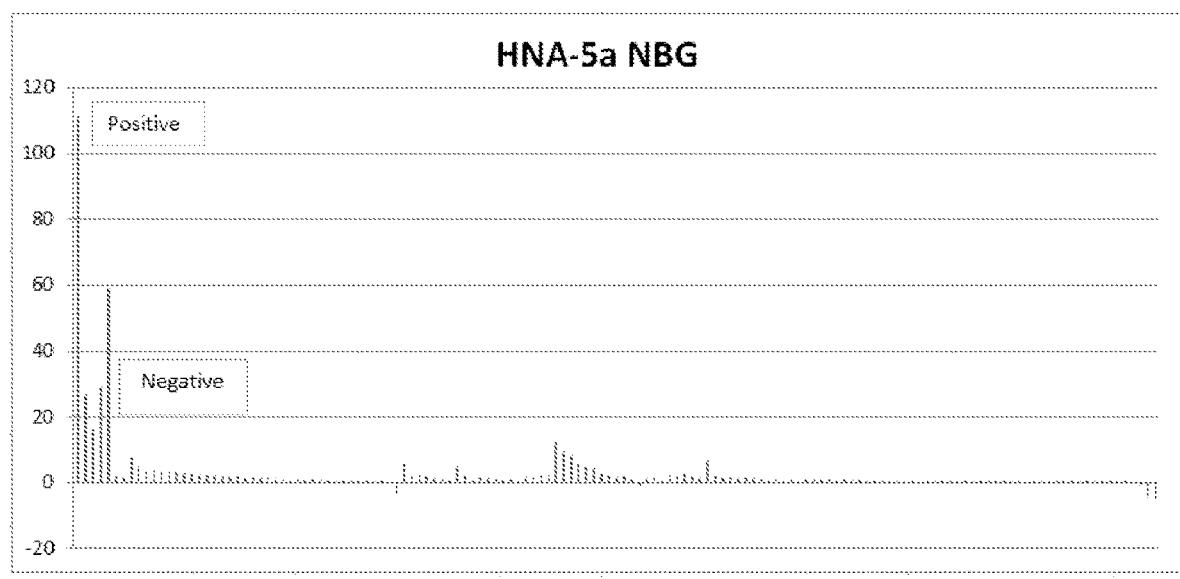
FIG. 9 depicts the detection sensitivity for HNA-5a specific antibodies.

The detection ratio for HNA-5a was examined using purified full length HNA-5a proteins. The wild type proteins were coated on microbeads. The negative sera (#LSNC) was defined as the human sera that does not have positive reaction against any HLA or HNA proteins and the HNA-5a positive sera was affirmed by neutralphil agglutination assay. The microbeads were incubated with the sera and analyzed as described in Example 1. The reaction pattern were compared and provided in Table 5 (based on 6 tests). The difference in detection sensitivity between HNA-3a positive sera and negative sera is provided in FIG. 9.

TABLE 7

The detection ration of HNA-5a molecules with HNA-4a positive and HNA-5 negative sera

|  | Purified HNA-5a protein |
| --- | --- |
| Negative mouse IgG | 1 |
| Positive mouse IgG (#ICRF44) | 3 ± 1 |
| Positive mouse IgG (#HB249) | 3 ± 1 |
| Positive mouse IgG (#TS1/18) | 5 ± 2 |

---

What is claimed:

1. A purified Fc gamma receptor type IIIb polypeptide comprising the amino acid sequence of SEQ ID NO: 1, wherein the amino acid sequence of SEQ ID NO: 1 comprises a substitution wherein leucine at residue 136 of SEQ ID NO: 1 is substituted with alanine (L136A).

2. A solid substrate on which one or more of the polypeptides of claim 1 are attached to the solid substrate.

3. A kit comprising the polypeptide of claim 1 and optionally comprising a polypeptide comprising the amino acid sequence of SEQ ID NO: 1.

4. The kit of claim 3 further comprising one or more polypeptides selected from the group consisting of CD177 polypeptide, choline transporter-like protein 2 (CTL2) polypeptide, CD11b polypeptide, CD11a polypeptide, an HLA antigen and a MHC class I polypeptide-related sequence A (MICA) antigen.

5. An antigenic peptide comprising the amino acid sequence of SEQ ID NO: 16.

6. A kit comprising the antigenic peptide of claim 5.

* * * * *

SEQUENCE LISTING

```
<160> NUMBER OF SEQ ID NOS: 33

<210> SEQ ID NO 1
<211> LENGTH: 233
<212> TYPE: PRT
<213> ORGANISM: Homo sapiens

<400> SEQUENCE: 1

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80
```

```
Val Asn Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
        100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
                195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 2
<211> LENGTH: 8
<212> TYPE: PRT
<213> ORGANISM: Homo sapiens

<400> SEQUENCE: 2

Trp Lys Asn Thr Ala Leu His Lys
1               5

<210> SEQ ID NO 3
<211> LENGTH: 5
<212> TYPE: PRT
<213> ORGANISM: Homo sapiens

<400> SEQUENCE: 3

Tyr Phe His His Asn
1               5

<210> SEQ ID NO 4
<211> LENGTH: 7
<212> TYPE: PRT
<213> ORGANISM: Homo sapiens

<400> SEQUENCE: 4

Leu Val Gly Ser Lys Asn Val
1               5

<210> SEQ ID NO 5
<211> LENGTH: 233
<212> TYPE: PRT
<213> ORGANISM: Homo sapiens

<400> SEQUENCE: 5

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45
```

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Phe Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 6
<211> LENGTH: 8
<212> TYPE: PRT
<213> ORGANISM: Homo sapiens

<400> SEQUENCE: 6

Phe Lys Asn Thr Ala Leu His Lys
1               5

<210> SEQ ID NO 7
<211> LENGTH: 233
<212> TYPE: PRT
<213> ORGANISM: Homo sapiens

<400> SEQUENCE: 7

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Arg Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 8
<211> LENGTH: 8
<212> TYPE: PRT
<213> ORGANISM: Homo sapiens

<400> SEQUENCE: 8

Trp Arg Asn Thr Ala Leu His Lys
1               5

<210> SEQ ID NO 9
<211> LENGTH: 233
<212> TYPE: PRT
<213> ORGANISM: Homo sapiens

<400> SEQUENCE: 9

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Phe Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

```
Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 10
<211> LENGTH: 8
<212> TYPE: PRT
<213> ORGANISM: Homo sapiens

<400> SEQUENCE: 10

```
Trp Lys Phe Thr Ala Leu His Lys
1               5
```

<210> SEQ ID NO 11
<211> LENGTH: 233
<212> TYPE: PRT
<213> ORGANISM: Homo sapiens

<400> SEQUENCE: 11

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Trp Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 12
<211> LENGTH: 8
<212> TYPE: PRT
<213> ORGANISM: Homo sapiens

<400> SEQUENCE: 12

Trp Lys Asn Trp Ala Leu His Lys
1               5

<210> SEQ ID NO 13
<211> LENGTH: 233
<212> TYPE: PRT
<213> ORGANISM: Homo sapiens

<400> SEQUENCE: 13

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Asp Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 14
<211> LENGTH: 8
<212> TYPE: PRT
<213> ORGANISM: Homo sapiens

<400> SEQUENCE: 14

Trp Lys Asn Thr Asp Leu His Lys
1               5

<210> SEQ ID NO 15
<211> LENGTH: 233
<212> TYPE: PRT
<213> ORGANISM: Homo sapiens

<400> SEQUENCE: 15

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro

-continued

```
                20                  25                  30
Gln Trp Tyr Ser Val Leu Glu Lys Asp Ser Val Thr Leu Lys Cys Gln
            35                  40                  45
Gly Ala Tyr Ser Pro Glu Asp Asn Ser Thr Gln Trp Phe His Asn Glu
 50                  55                  60
Ser Leu Ile Ser Ser Gln Ala Ser Ser Tyr Phe Ile Asp Ala Ala Thr
 65                  70                  75                  80
Val Asn Asp Ser Gly Glu Tyr Arg Cys Gln Thr Asn Leu Ser Thr Leu
                85                  90                  95
Ser Asp Pro Val Gln Leu Glu Val His Ile Gly Trp Leu Leu Leu Gln
            100                 105                 110
Ala Pro Arg Trp Val Phe Lys Glu Glu Asp Pro Ile His Leu Arg Cys
        115                 120                 125
His Ser Trp Lys Asn Thr Ala Ala His Lys Val Thr Tyr Leu Gln Asn
    130                 135                 140
Gly Lys Asp Arg Lys Tyr Phe His His Asn Ser Asp Phe His Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Ser Pro Pro Gly Tyr Gln
        195                 200                 205
Val Ser Phe Cys Leu Val Met Val Leu Leu Phe Ala Val Asp Thr Gly
    210                 215                 220
Leu Tyr Phe Ser Val Lys Thr Asn Ile
225                 230
```

<210> SEQ ID NO 16
<211> LENGTH: 8
<212> TYPE: PRT
<213> ORGANISM: Homo sapiens

<400> SEQUENCE: 16

```
Trp Lys Asn Thr Ala Ala His Lys
 1               5
```

<210> SEQ ID NO 17
<211> LENGTH: 233
<212> TYPE: PRT
<213> ORGANISM: Homo sapiens

<400> SEQUENCE: 17

```
Met Trp Gln Leu Leu Leu Pro Thr Ala Leu Leu Leu Leu Val Ser Ala
 1               5                  10                  15
Gly Met Arg Thr Glu Asp Leu Pro Lys Ala Val Val Phe Leu Glu Pro
                20                  25                  30
Gln Trp Tyr Ser Val Leu Glu Lys Asp Ser Val Thr Leu Lys Cys Gln
            35                  40                  45
Gly Ala Tyr Ser Pro Glu Asp Asn Ser Thr Gln Trp Phe His Asn Glu
 50                  55                  60
Ser Leu Ile Ser Ser Gln Ala Ser Ser Tyr Phe Ile Asp Ala Ala Thr
 65                  70                  75                  80
Val Asn Asp Ser Gly Glu Tyr Arg Cys Gln Thr Asn Leu Ser Thr Leu
                85                  90                  95
Ser Asp Pro Val Gln Leu Glu Val His Ile Gly Trp Leu Leu Leu Gln
```

```
            100                 105                 110
Ala Pro Arg Trp Val Phe Lys Glu Glu Asp Pro Ile His Leu Arg Cys
        115                 120                 125

His Ser Phe Lys Asn Thr Ala Leu Tyr Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 18
<211> LENGTH: 8
<212> TYPE: PRT
<213> ORGANISM: Homo sapiens

<400> SEQUENCE: 18

Phe Lys Asn Thr Ala Leu Tyr Lys
1               5

<210> SEQ ID NO 19
<211> LENGTH: 233
<212> TYPE: PRT
<213> ORGANISM: Homo sapiens

<400> SEQUENCE: 19

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Thr Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
```

```
              180                 185                 190
Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 20
<211> LENGTH: 8
<212> TYPE: PRT
<213> ORGANISM: Homo sapiens

<400> SEQUENCE: 20

Trp Lys Asn Thr Ala Leu His Thr
1               5

<210> SEQ ID NO 21
<211> LENGTH: 233
<212> TYPE: PRT
<213> ORGANISM: Homo sapiens

<400> SEQUENCE: 21

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe Tyr His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 22
<211> LENGTH: 5
<212> TYPE: PRT
```

<213> ORGANISM: Homo sapiens

<400> SEQUENCE: 22

Tyr Phe Tyr His Asn
1               5

<210> SEQ ID NO 23
<211> LENGTH: 233
<212> TYPE: PRT
<213> ORGANISM: Homo sapiens

<400> SEQUENCE: 23

Met Trp Gln Leu Leu Pro Thr Ala Leu Leu Leu Val Ser Ala
1               5                   10                  15

Gly Met Arg Thr Glu Asp Leu Pro Lys Ala Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His Glu Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 24
<211> LENGTH: 5
<212> TYPE: PRT
<213> ORGANISM: Homo sapiens

<400> SEQUENCE: 24

Tyr Phe His Glu Asn
1               5

<210> SEQ ID NO 25
<211> LENGTH: 233
<212> TYPE: PRT
<213> ORGANISM: Homo sapiens

<400> SEQUENCE: 25

```
Met Trp Gln Leu Leu Leu Pro Thr Ala Leu Leu Leu Val Ser Ala
1               5                  10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Asp Arg Lys Tyr Ala Ala Ala Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230

<210> SEQ ID NO 26
<211> LENGTH: 5
<212> TYPE: PRT
<213> ORGANISM: Homo sapiens

<400> SEQUENCE: 26

Tyr Ala Ala Ala Asn
1               5

<210> SEQ ID NO 27
<211> LENGTH: 233
<212> TYPE: PRT
<213> ORGANISM: Homo sapiens

<400> SEQUENCE: 27

Met Trp Gln Leu Leu Leu Pro Thr Ala Leu Leu Leu Val Ser Ala
1               5                  10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80
```

-continued

```
Val Asn Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
        100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Ala
                165                 170                 175

Ala Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

<210> SEQ ID NO 28
<211> LENGTH: 7
<212> TYPE: PRT
<213> ORGANISM: Homo sapiens

<400> SEQUENCE: 28

```
Leu Ala Ala Ser Lys Asn Val
1               5
```

<210> SEQ ID NO 29
<211> LENGTH: 233
<212> TYPE: PRT
<213> ORGANISM: Homo sapiens

<400> SEQUENCE: 29

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
        100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160
```

```
Lys Ala Thr Leu Lys Asp Ser Gly Ser Tyr Phe Cys Arg Gly Leu Val
            165                 170                 175

Gly Ser Leu Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230

<210> SEQ ID NO 30
<211> LENGTH: 7
<212> TYPE: PRT
<213> ORGANISM: Homo sapiens

<400> SEQUENCE: 30

Leu Val Gly Ser Leu Asn Val
1               5

<210> SEQ ID NO 31
<211> LENGTH: 233
<212> TYPE: PRT
<213> ORGANISM: Homo sapiens

<400> SEQUENCE: 31

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65              70                  75                  80

Val Asn Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
            165                 170                 175

Gly Ser Lys Asn Tyr Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230
```

<210> SEQ ID NO 32
<211> LENGTH: 7
<212> TYPE: PRT
<213> ORGANISM: Homo sapiens

<400> SEQUENCE: 32

Leu Val Gly Ser Lys Asn Tyr
1               5

<210> SEQ ID NO 33
<211> LENGTH: 887
<212> TYPE: DNA
<213> ORGANISM: Homo sapiens

<400> SEQUENCE: 33

```
tctttggtga cttgtccact ccagtgtggc atcatgtggc agctgctcct cccaactgct      60
ctgctacttc tagtttcagc tggcatgcgg actgaagatc tcccaaaggc tgtggtgttc     120
ctggagcctc aatggtacag cgtgcttgag aaggacagtg tgactctgaa gtgccaggga     180
gcctactccc ctgaggacaa ttccacacag tggtttcaca atgagagcct catctcaagc     240
caggcctcga gctacttcat tgacgctgcc acagtcaacg acagtggaga gtacaggtgc     300
cagacaaacc tctccaccct cagtgacccg gtgcagctag aagtccatat cggctggctg     360
ttgctccagg cccctcggtg ggtgttcaag gaggaagacc ctattcacct gaggtgtcac     420
agctggaaga acactgctct gcataaggtc acatatttac agaatggcaa agacaggaag     480
tattttcatc ataattctga cttccacatt ccaaaagcca cactcaaaga tagcggctcc     540
tacttctgca gggggcttgt tgggagtaaa aatgtgtctt cagagactgt gaacatcacc     600
atcactcaag gtttggcagt gtcaaccatc tcatcattct ctccacctgg gtaccaagtc     660
tctttctgct tggtgatggt actccttttt gcagtggaca caggactata tttctctgtg     720
aagacaaaca tttgaagctc aacaagagac tggaaggacc ataaacttaa atggagaaag     780
gaccctcaag acaaatgacc cccatcccat gggagtaata agagcagtgg cagcagcatc     840
tctgaacatt tctctggatt tgcaacccca tcatcctcag gcctctc                   887
```